United States Patent [19]
Nishi et al.

[11] Patent Number: 5,998,437
[45] Date of Patent: Dec. 7, 1999

[54] BENZIMIDAZOLE DERIVATIVES

[75] Inventors: Takao Nishi; Seiji Sato, both of Tokushima; Takeshi Nagatani, Kurume; Hirotaka Yukawa, Naruto; Nobuyuki Koga, Tokushima; Masahiro Saito, Naruto; Shinji Yoshinaga, Tokushima, all of Japan

[73] Assignee: Otsuka Pharmaceutical Co., Ltd., Tokyo, Japan

[21] Appl. No.: 08/793,312

[22] PCT Filed: Jul. 3, 1996

[86] PCT No.: PCT/JP96/01841

§ 371 Date: Mar. 6, 1997

§ 102(e) Date: Mar. 6, 1997

[87] PCT Pub. No.: WO97/03070

PCT Pub. Date: Jan. 30, 1997

[30] Foreign Application Priority Data

Jul. 7, 1995 [JP] Japan ..................... 7-171807

[51] Int. Cl.⁶ ............... A01N 43/42; A01N 43/52; C07D 215/38; C07D 235/04
[52] U.S. Cl. ............... 514/314; 514/387; 514/391; 546/161; 548/223; 548/305.1; 548/308.4
[58] Field of Search ............... 546/161; 548/305.1, 548/308.4, 223; 514/391, 387, 314

[56] References Cited

U.S. PATENT DOCUMENTS

| | | | |
|---|---|---|---|
| 4,551,421 | 11/1985 | Sugimoto et al. | 430/509 |
| 4,886,803 | 12/1989 | Sueda et al. | 514/252 |
| 4,994,477 | 2/1991 | Kempf et al. | 514/359 |
| 5,098,924 | 3/1992 | Poss | 514/397 |

FOREIGN PATENT DOCUMENTS

| | | |
|---|---|---|
| 0 407 217 A1 | 1/1991 | European Pat. Off. . |
| 0 560 407 A1 | 9/1993 | European Pat. Off. . |
| 61-167952 | 7/1986 | Japan . |
| 62-246546 | 10/1987 | Japan . |
| 64-65551 | 3/1989 | Japan . |
| 1-96645 | 4/1989 | Japan . |
| 2-306916 | 12/1990 | Japan . |
| 4-346974 | 2/1992 | Japan . |
| 5-222000 | 8/1993 | Japan . |
| 7-133224 | 5/1995 | Japan . |
| WO 93/07124 | 4/1993 | WIPO . |
| WO 94/22855 | 10/1994 | WIPO . |

OTHER PUBLICATIONS

O. Teruo et al., "Preparation of Benzylbenzimidazoles as c–GMP Phosphodiesterase Inhibitiors", Chemical Abstracts, 120:15:191719 (1994).

Sueda et al., Chemical Abstract V of 108 No. 167472,.

*Primary Examiner*—John Kight
*Assistant Examiner*—Raymond Covington
*Attorney, Agent, or Firm*—Finnegan, Henderson, Farabow, Garrett & Dunner, L.L.P.

[57] ABSTRACT

The present invention provides novel benzimidazole derivatives or salts thereof represented by the general formula,

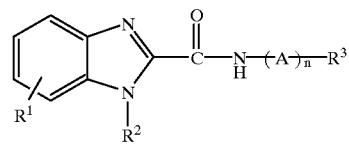

wherein $R^1$ is a hydrogen atom or a halogen atom; $R^2$ is a phenyl-lower alkyl group; $R^3$ is a heterocyclic group selected from the group consisting of an indolyl group, indolinyl group, 1H-indazolyl group, 2(1H)-quinolinonyl group, 3,4-dihydro-2(1H)-quinolinonyl group and 1,4-benzoxazinyl group; A is a lower alkylene group; n is 0 or 1.

The benzimidazole derivatives or salts of the present invention are effective agents for treating various arteriosclerotic diseases.

42 Claims, No Drawings

BENZIMIDAZOLE DERIVATIVES

This application is a 371 of PCT/JP9601841 filed Jul. 3, 1996.

TECHNICAL FIELD

The present invention relates to novel benzimidazole derivatives and salts thereof.

BACKGROUND ART

Proliferation of the smooth muscle cells of the blood vessel induces hypertrophy of the intima of the blood vessel and, from a long-term view point, it causes, arteriosclelerotic diseases such as myocardial infarction, cerebral infarction and the like. Moreover, from a short-term view point, it induces reobstruction of the blood vessel after treatments of percutaneous transluminal coronary angioplasty (PTCA), stent and/or aterectomy. In consideration of the present situation, the therapeutic effects of conventional medicines used therefor are thought of as within certain limits, because they are classified as agents of indirectly effective for curing the diseases induced by the promotion factors of hypertrophy of the interim, for example hyperlipidemia, hypertension and the like. Therefore, development of essentially effective medicines therefor have been eagerly expected.

Generally, it is known that proliferation of the smooth muscle cells is related to the influence of cyclic guanosine 3',5'-monophosphate (cGMP). In this connection, pharmaceutical preparations of nitro group-containing compound known as coronary vasodilators activate the enzymatic activity of guanylate cyclase, and accentuate the production of cGMP, and also inhibit the proliferation of the cells. However, the pharmaceutical preparations of nitro group-containing compound are scarecely used for treatment of arteriosclerotic diseases which need to be administered for a long period of time, because the effect of the pharmaceutical preparations of nitro group-containing compound can be sustained only for a quite short time, and when they are administered repeatedly, then the tolerance against said pharmaceutical preparations may be occurred. On the other hand, in recent years, there have been reported several pharmaceutical preparations which can increase the concentration of cGMP by inhibiting the enzymatic activity of the enzyme [i.e., cGMP-PDE (cGMP-phosphodiesterase)] for decomposition of cGMP. However, there have not been suggested the activity for inhibiting proliferation of the smooth muscle cells performed by pharmaceutical preparations. The guanine derivative which was reported recently in an academic conference (IBC's International Conference on RESTENOSIS, 1994, U. S. A.) is the only known compound having both effects for inhibiting the enzymatic activity of cGMP-PDE and for inhibiting proliferation of the smooth muscle cells.

In consideration of the present status of such pharmacotherapy, and referring to the fact that cGMP relates to proliferation of the smooth muscle cells of the blood vessel, the present inventors have made an extensive research work regarding pharmaceutical preparations having the activity for inhibiting proliferation of the smooth muscle cells of the blood vessel which acts directly to the cells thereof, and can be used as the essential agent for treating arteriosclerotic diseases.

As the results, the present inventors have found the fact that the objective compounds, having the activity for inhibiting proliferation of the smooth muscle cells of the blood vessel, are existed among benzimidazole derivatives having property for inhibiting the enzymatic activity of cGMP PDE, thus the present invention has been completed.

Related art references which disclose compounds having chemical structural formulas similar to those disclose in the present invention are JP-A-2-306916, U.S. Pat. No. 4,886,803, U.S. Pat. No. 4,551,421, JP-A-62-246546, JP-A-4-346974, JP-A-61-167952, U.S. Pat. No. 4,994,477, U.S. Pat. No. 5,098,924, EP-A1-0560407, EP-A1-0407217, JP-A-64-65551, JP-A-1-96645, and JP-A-7-133224, however, those references neither disclose nor suggest benzimidazole derivatives of the present invention, and do not touch on inhibition of the enzymatic activity of cGMP PDE at all which benzimidazole derivatives of the present invention possess.

Furthermore, references JP-A-5-222000, WO-A-93-07124, and WO-A-94-22855 disclose structural similar compounds having inhibition of the enzymatic activity of cGMP PDE, however, those references neither disclose nor suggest benzimidazole derivatives of the present invention.

DISCLOSURE OF THE INVENTION

Benzimidazole derivatives of the present invention are novel compounds which have not been reported in any literature, and are represented by the general formula (1) as follows:

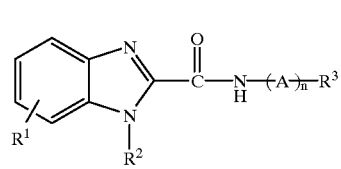

(1)

[wherein

R$^1$ is a hydrogen atom or a halogen atom;

R$^2$ is a phenyl-lower alkyl group;

R$^3$ is a heterocyclic group selected from the group consisting of an indolyl group, indolinyl group, 1H-indazolyl group, 2(1H)-quinolinonyl group, 3,4-dihydro-2(1H)-quinolinonyl group and 3,4-dihydro-1,4(2H)-benzoxazinyl group, said heterocyclic group may have 1 to 3 substituents selected from the group consisting of: a group of the formula —B—R$^4$, (B is a lower alkylene group; R$^4$ is a 5- to 11-membered saturated or unsaturated heterocyclic group of single ring or binary ring, having 1 to 4 hetero atoms selected from the group consisting of a nitrogen atom, oxygen atom and sulfur atom, (said heterocyclic group may have 1 to 3 substituents selected from the group consisting of a halogen atom, a lower alkyl group, a lower alkoxy group and oxo group) or a group of the formula —NR$^5$R$^6$ (R$^5$ and R$^6$ are each the same or different, and a hydrogen atom, a lower alkyl group, a cycloalkyl group, a pyridylcarbonyl group, an isoxazolylcarbonyl group which may have 1 to 3 lower alkyl groups as the substituents, a pyrrolylcarbonyl group or an amino-substituted lower alkyl group which may have a lower alkyl group as the substituent; further R$^5$ and R$^6$ may form 5- to 6-membered saturated heterocyclic group by combining to each other, together with the adjacent nitrogen atom being bonded thereto, further with or without other nitrogen atom or oxygen atom; said heterocyclic group may have 1 to 3 substituents selected from the group consisting of a hydroxy group and a phenyl group));

a lower alkenyl group; a lower alkoxycarbonyl group;
a phenoxy-lower alkyl group which may have cyano group as the substituents; a halogen-substituted lower alkyl group; and a lower alkoxycarbonyl-substituted lower alkyl group;
A is a lower alkylene group; and
n is 0 or 1.].

The benzimidazole derivatives of the present invention possess weak activity for inhibiting the enzymatic action of cAMP PDE, while they possess strong activity for inhibiting the enzymatic action selectively against cGMP PDE.

The benzimidazole derivatives of the present invention possess activity for inhibiting proliferation of the smooth muscle cells, especially they possess strong activity for inhibiting proliferation of the mesenchymal cells. The activity for inhibiting proliferation of the smooth muscle cells was determination by measuring the activity for inhibiting proliferation of rat A10 cell (in vitro), and confirmed. The rat A10 cell is a cell strain derived from smooth muscle of rat embryo thoracic aorta, and the biological property thereof is described in Exptl. Cell Ress. Vol. 98, (1976), pages 349–365, (B. W. Kimes and B. L. Brandt). The activity for inhibiting proliferation of the fibroblasts and mesangial cells were determined by measuring the activity for inhibiting proliferation of human fibroblasts or rat mesangial cells in place of rat A10 cell, by the procedure similar to that of described in the same literature, and confirmed strong activities for inhibition. The activity for inhibiting proliferating of T-cells was determined by procedure of the experiment as described in "Current Protocol in Immunology" Chapter 3, page 12 [compiled by Coligan, et al., (1991), (published by Willy Interscience)], and confirmed. As mentioned above, the benzimidazole derivatives of the present invention also possess immunosuppressive activity based on the activity for inhibiting proliferation of T-cells.

The benzimidazole derivatives of the present invention possess activity for inhibiting synthesis and secretion of collagen. Thus, the activity was confirmed by culturing human fibroblast and by method as described in Clin. Invest., Vol. 83, (1989), pages 1160–1167 (K. Mackay, et al.) and by applying assay method as described in Calcif. Tissue Int., Vol. 35, (1983), pages 542–548 (M. Kumegawa, et al.).

Furthermore, the benzimidazole derivatives of the present invention also possess antiinflammatory activity. In case of using as a drug for external use, the antiinflammatory activity of banzimidazole derivative was confirmed by the procedures of experiment as described in Agents Actions, Vol. 26, (1989), page 319 (Carlson, et al.) [Test animals and administration method were partly revised]. Said inflammatory activity of benzimidazole derivative of the present invention was confirmed in detail as described in (6) Determination of the activity for inhibiting TPA-induced inflammation as described later in this specification.

Proliferation of the smooth muscle cells of the blood vessel is the major cause of arteriosclerosis. [Nature Vol. 362, (1993), pages 801–809 (Russell Ross)]. Moreover, proliferation of fibroblast and synthesis and secretion of collagen are also the causes of arteriosclerosis. [Am. J. Pathol., Vol. 125, (1986), pages 191–207 (A. M. Gown, et al.)]. In the case of diabetes mellitus, the smooth muscle cells show tendency of abnormal proliferation. [Eu. J. Clin. Invest. Vol. 23, (1993), pages 84–90 (M. Kawano, et al.)]. Proliferation of fibroblast as well as synthesis and secretion of collagen induce pulmonary fibrosis. [Am. Rev. Respir. Dis., Vol 138, (1988), pages 703–708 (G. Raghu, et al.); and CHIRYOU-GAKU (Therapeutics), Vol. 28, (1994), pages 62–66, (Toshihiko Sakai, et al.). Inhibition of the enzymatic activity of cGMP PDE inhibits aggregation of platelets, as well as effective for prevention and treatment of allergy, asthma, psoriasis and formation of thrombus. [Trends Pharmacol. Sci., Vol. 12, (1991), pages 19–27 (C. D. Nicholson, et al.)]. Increase of the amount of cGMP lowers blood pressure. [Circ. Res., Vol. 74, (1994), pages 416–421 (A. Koller, et al.) and DOHMYAKU KOUKA NO BUNSHI IGAKU (Molecular Medicine of Arteriosclerosis) (compiled by Tohru Kita, 1994, published by YOHDO-SHA, pages 27–28 and 147–164)].

As explained above, according to the pharmacological activities performed by the benzimidazole derivatives of the present invention, they can be applied to prevention and treatment of various diseases for example, diseases related to cGMP, diseases induced by proliferation of the smooth muscle cells and fibroblast, diseases related to synthesis and secretion of collagen, and they can be further applied to prevention and treatment of skin diseases relating to immune and inflammation. As to these diseases, there can be exemplified, reobstruction of the blood vessel occurred after the treatments of PTCA, anginoplasy and operation of bypass, arteriosclerotic diseases [e.g., angina pectoris, myocardial infarction, cerebral infarction, cerebrovascular dementia, transient ischemic attack (TIA), disfunction of peripheral circulation, complication of diabetes mellitus, atherosclerosis, arteriolosclerosis, fibrous hypertrophy of artery and the like], cell proliferative diseases other than arteriosclerotic diseases (e.g., renal disease, asthma, bronchitis, proliferative dermatitis, keloidosis, hyperplastic scar, glaucoma and the like), pulmonary fibrosis, collagen disease, psoriasis, allergic diseases (especially, atopic dermatitis and chronic contactive dermatitis), other dermatitises, hypertension, organopathy induced by hypertension, cardiac failure, hypercardia and the like.

The benzimidazole derivatives of the present invention can be administered orally and non-orally by making them as in the form of suitable pharmaceutical preparations, and in case of apply to dermatic diseases, a pharmaceutical preparation made for external use can be applied by coating directly onto the diseased part. The effectiveness of the benzimidazole derivatives of the present invention applied in the form of pharmaceutical preparations for external use was confirmed by conducting experiments as described in J. Dermtol. Sci., Vol. 8, (1994), page 54 (Kitagaki, et al.) and Agents Actions, Vol. 26, (1989), page 319 (Carlson, et al.). [Animal test and method of administration were partly revided.] Detailed explanation relating to activity for inhibiting TPA-induced edema will be disclosed in Pharmacological Test (6), as mentioned later in this specification. Models in Dermatology, Vol. 1, pages 50–58 [(complied by H. I. Maibach, N. J. Lowe) (published by Krager, Basel) 1985] describes that the experiment as described in the latter literature (Agents Actions by Carlson, et al.) is a model of psoriasis.

As can be seen from the result of experiment conducted by using rat carotid paratripsis model [Am. J. Pathol., Vol. 141, (1992), pages 685–690 (U. Zeymer, et al.) the benzimidazole derivatives of the present invention are effective not only in vitro test but also in vivo test.

In case of oral administration, the benzimidazole derivatives of the present invention can be attained to keep blood concentration sufficient to manifestation of pharmacological effect, and the number of oral administration per day can be set as small number, because the duration of blood concentration and action time thereof can be kept for quite long time.

The benzimidazole derivatives of the present invention are characterized by having quite weak activity of acute vasodepression effect, systolic potentiation effect and cardiac rate increasing effect at the dosage of showing inhibitory effect of cGMP PDE, and at the dosage of showing inhibitory effect of proliferation of the smooth muscle cells.

The benzimidazole derivatives of the present invention do not show strong toxicity even though they are administered for short-term or administered continuously for long-term.

As to the benzimidazole derivatives of the present invention represented by the general formula (1), there are various types of derivatives are included as follows:

① Benzimidazol derivatives or salts thereof represented by the general formula (1), wherein $R^1$ is a hydrogen atom; $R^2$ is the same as defined in the general formula (1) as mentioned above; n is 0, and $R^3$ is an indolyl group (wherein the substituents of the indolyl group are the same as defined in the general formula (1) as mentioned above).

② Benzimidazol derivatives or salts thereof represented by the general formula (1), wherein $R^1$ is a hydrogen atom; $R^2$ is the same as defined in the general formula (1) as mentioned above; n is 0, and $R^3$ is an indolinyl group (wherein the substituents of the indolinyl group are the same as defined in the general formula (1) as mentioned above).

③ Benzimidazol derivatives or salts thereof represented by the general formula (1), wherein $R^1$ is a hydrogen atom; $R^2$ is the same as defined in the general formula (1) as mentioned above; n is 0, and $R^3$ is a 1H-indazolyl group (wherein the substituents of the 1H-indazolyl group are the same as defined in the general formula (1) as mentioned above).

④ Benzimidazol derivatives or salts thereof represented by the general formula (1), wherein $R^1$ is a hydrogen atom; $R^2$ is the same as defined in the general formula (1) as mentioned above; n is 0, and $R^3$ is 2(1H)-quinolinonyl group (wherein the substituents of the 2(1H)-quinolinonyl group are the same as defined in the general formula (1) as mentioned above).

⑤ Benzimidazol derivatives or salts thereof represented by the general formula (1), wherein $R^1$ is a hydrogen atom; $R^2$ is the same as defined in the general formula (1) as mentioned above; n is 0, and $R^3$ is 3,4-dihydro-2(1H)-quinolinonyl group (wherein the substituents of the 3,4-dihydro-2(1H)-quinolinonyl group are the same as defined in the general formula (1) as mentioned above).

⑥ Benzimidazol derivatives or salts thereof represented by the general formula (1), wherein $R^1$ is a hydrogen atom; $R^2$ is the same as defined in the general formula (1) as mentioned above; n is 0, and $R^3$ is 3,4-dihydro-1,4(2H)-benzoxazinyl group (wherein the substituents of the 3,4-dihydro-1,4(2H)-benzoxazinyl group are the same as defined in the general formula (1) as mentioned above).

⑦ Benzimidazol derivatives or salts thereof represented by the general formula (1), wherein $R^1$ is a halogen atom; $R^2$ is the same as defined in the general formula (1) as mentioned above; n is 0, and $R^3$ is an indolyl group (wherein the substituents of the indolyl group are the same as defined in the general formula (1) as mentioned above).

⑧ Benzimidazol derivatives or salts thereof represented by the general formula (1), wherein $R^1$ is a halogen atom; $R^2$ is the same as defined in the general formula (1) as mentioned above; n is 0, and $R^3$ is an indolinyl group (wherein the substituents of the indolinyl group are the same as defined in the general formula (1) as mentioned above).

⑨ Benzimidazol derivatives or salts thereof represented by the general formula (1), wherein $R^1$ is a halogen atom; $R^2$ is the same as defined in the general formula (1) as mentioned above; n is 0, and $R^3$ is a 1H-indazolyl group (wherein the substituents of the 1H-indazolyl group are the same as defined in the general formula (1) as mentioned above).

⑩ Benzimidazol derivatives or salts thereof represented by the general formula (1), wherein $R^1$ is a halogen atom; $R^2$ is the same as defined in the general formula (1) as mentioned above; n is 0, and $R^3$ is a 2(1H)-quinolinonyl group (wherein the substituents of the 2(1H)-quinolinonyl group are the same as defined in the general formula (1) as mentioned above).

⑪ Benzimidazol derivatives or salts thereof represented by the general formula (1), wherein $R^1$ is a halogen atom; $R^2$ is the same as defined in the general formula (1) as mentioned above; n is 0, and $R^3$ is a 3,4-dihydro-2(1H)-quinolinonyl group (wherein the substituents of the 3,4-dihydro-2(1H)-quinolinonyl group are the same as defined in the general formula (1) as mentioned above).

⑫ Benzimidazol derivatives or salts thereof represented by the general formula (1), wherein $R^1$ is a halogen atom; $R^2$ is the same as defined in the general formula (1) as mentioned above; n is 0, and $R^3$ is a 3,4-dihydro-1,4(2H)-benzoxazinyl group (wherein the substituents of the 3,4-dihydro-1,4(2H)-benzoxazinyl group are the same as defined in the general formula (1) as mentioned above).

⑬ Benzimidazol derivatives or salts thereof represented by the general formula (1), wherein $R^1$ is a hydrogen atom; $R^2$ is the same as defined in the general formula (1) as mentioned above; n is 1, and $R^3$ is an indolyl group (wherein the substituents of the indolyl group are the same as defined in the general formula (1) as mentioned above).

⑭ Benzimidazol derivatives or salts thereof represented by the general formula (1), wherein $R^1$ is a hydrogen atom; $R^2$ is the same as defined in the general formula (1) as mentioned above; n is 1, and $R^3$ is an indolinyl group (wherein the substituents of the indolinyl group are the same as defined in the general formula (1) as mentioned above).

⑮ Benzimidazol derivatives or salts thereof represented by the general formula (1), wherein $R^1$ is a hydrogen atom; $R^2$ is the same as defined in the general formula (1) as mentioned above; n is 1, and $R^3$ is a 1H-indazolyl group (wherein the substituents of the 1H-indazolyl group are the same as defined in the general formula (1) as mentioned above).

⑯ Benzimidazol derivatives or salts thereof represented by the general formula (1), wherein $R^1$ is a hydrogen atom; $R^2$ is the same as defined in the general formula (1) as mentioned above; n is 1, and $R^3$ is a 2(1H)-quinolinonyl group (wherein the substituents of the 2(1H)-quinolinolyl group are the same as defined in general formula (1) as mentioned above).

⑰ Benzimidazol derivatives or salts thereof represented by the general formula (1), wherein $R^1$ is a hydrogen atom; $R^2$ is the same as defined in the general formula (1) as mentioned above; n is 1, and $R^3$ is a 3,4-dihydro-2(1H)-quinolinonyl group (wherein the substituents of the 3,4-dihydro-2(1H)-quinolinonyl group are the same as defined in the general formula (1) as mentioned above).

⑱ Benzimidazol derivatives or salts thereof represented by the general formula (1), wherein $R^1$ is a hydrogen atom; $R^2$ is the same as defined in the general formula (1) as mentioned above; n is 1, and R3 is a 3,4-dihydro-1,4(2H)-benzoxazinyl group (wherein the substituents of the 3,4-dihydro-1,4(2H)-benzoxazinyl group are the same as defined in the general formula (1) as mentioned above).

⑲ Benzimidazol derivatives or salts thereof represented by the general formula (1), wherein $R^1$ is a halogen atom; $R^2$ is the same as defined in the general formula (1) as mentioned above; n is 1, and $R^3$ is an indolyl group (wherein the substituents of the indolyl group are the same as defined in the general formula (1) as mentioned above).

⑳ Benzimidazol derivatives or salts thereof represented by the general formula (1), wherein $R^1$ is a halogen atom; $R^2$ is the same as defined in the general formula (1) as mentioned above; n is 1, and $R^3$ is an indolinyl group (wherein the substituents of the indolinyl group are the same as defined in the general formula (1) as mentioned above).

㉑ Benzimidazol derivatives or salts thereof represented by the general formula (1), wherein $R^1$ is a halogen atom; $R^2$ is the same as defined in the general formula (1) as mentioned above; n is 1, and $R^3$ is a 1H-indazolyl group (wherein the substituents of the 1H-indazolyl group are the same as defined in the general formula (1) as mentioned above).

㉒ Benzimidazol derivatives or salts thereof represented by the general formula (1), wherein $R^1$ is a halogen atom; $R^2$ is the same as defined in the general formula (1) as mentioned above; n is 1, and $R^3$ is a 2(1H)-quinolinonyl group (wherein the substituents of the 2(1H)-quinolinonyl group are the same as defined in the general formula (1) as mentioned above).

㉓ Benzimidazol derivatives or salts thereof represented by the general formula (1), wherein $R^1$ is a halogen atom; $R^2$ is the same as defined in the general formula (1) as mentioned above; n is 1, and $R^3$ is a 3,4-dihydro-2(1H)-quinolinonyl group (wherein the substituents of 3,4-dihydro-2(1H)-quinolinonyl group are the same as defined in the general formula (1) as mentioned above).

㉔ Benzimidazol derivatives or salts thereof represented by the general formula (1), wherein $R^1$ is a halogen atom; $R^2$ is the same as defined in the general formula (1) as mentioned above; n is 1, and $R^3$ is a 3,4-dihydro-1,4(2H)-benzoxazinyl group (wherein the substituents of 3,4-dihydro-1,4(2H)-benzoxazinyl group are the same as defined in the general formula (1) as mentioned above).

The concrete examples of various substituents as defined in $R^1$, $R^2$, $R^3$, A, B, $R^4$, $R^5$ and $R^6$ as shown in the general formula (1) are as follows.

As to the halogen atom, such as a fluorine atom, a chlorine atom, a bromine atom and iodine atom can be exemplified.

As to the phenyl-lower alkyl group, a phenyl-alkyl group in which the alkyl moiety is a straight- or branched-chain alkyl group having 1 to 6 carbon atoms, and said alkyl group having 1 to 2 phenyl groups, such as a benzyl, 2-phenylethyl, 1-phenylethyl, 3-phenyl-propyl, 4-phenylbutyl, 5-phenylpentyl, 6-phenylhexyl, 1,1-dimethyl-2-phenylethyl, 2-methyl-3-phenylpropyl, diphenylmethyl and 2,2-diphenylethyl groups can be exemplified.

As to the lower alkylene group, a straight- or branched-chain alkylene group having 1 to 6 carbon atoms, such as a methylene, ethylene, trimethylene, 2-methyltrimethylene, 2,2-dimethyltrimethylene, 1-methyltrimethylene, methylmethylene, ethylmethylene, tetramethylene, pentamethylene and hexamethylene groups can be exemplified.

As to the 5- to 11-membered saturated or unsaturated heterocyclic group of single ring or binary ring having 1 to 4 nitrogen atoms, oxygen atoms or sulfur atoms as the hetero atoms, such as pyrrolidinyl, piperidinyl, piperazinyl, morpholino, thiomorpholino, pyridyl, homopiperazinyl, 1,2,5,6-tetrahydropyridyl, thienyl, quinolinyl, 1,4-dihydroquinolinyl, benzothiazolyl, pyrazinyl, pyrimidinyl, pyridazinyl, pyrrolyl, carbostyril, 3,4-dihydrocarbostyril, 1,2,3,4-tetrahydroquinolinyl, indolyl, isoindolyl, indolinyl, benzimidazolyl, benzoxazolyl, imidazolidinyl, isoquinolinyl, quinazolidinyl, 1,2,3,4-tetrahydroisoquinolinyl, 1,2-dihydroisoquinolinyl, quinoxalinyl, cinnolinyl, phthalazinyl, 1,2,3,4-tetrazolyl, 1,2,4-triazolyl, chromanyl, isoindolinyl, isochromanyl, pyrazolyl, imidazolyl, pyrazolidinyl, imidazo[1,2-a]pyridyl, benzofuryl, 2,3-dihydrobenzo[b]furyl, benzothienyl, 1-azacycloheptyl, 4H-chromenyl, 1H-indazolyl, 2-imidazolinyl, 2-pyrrolinyl, furyl, oxazolyl, oxazolidinyl, isoxazolyl, thiazolyl, isothiazolyl, pyranyl, pyrazolidinyl, 2-pyrazolinyl, quinuclidinyl, 1,4-benzoxazinyl, 3,4-dihydro-2H-1,4-benzoxazinyl, 3,4-dihydro-2H-1,4-benzothiazinyl, 1,4-benzothiazinyl, 1,2,3,4-tetrahydroquinoxalinyl, 1,3-dithia-2,4-dihydronaphthalenyl, tetrahydro-1,3-oxazinyl, tetrahydroxazolyl and 1,4-dithianaphthalenyl groups can be exemplified.

As to the heterocyclic group having 1 to 3 substituents selected from the group consisting of a lower alkyl group, a lower alkoxy group, a halogen atom and an oxo group, a heterocyclic group having 1 to 3 substituents selected from the group consisting of a straight- or branched-chain alkyl group having 1 to 6 carbon atoms, a straight- or branched-chain alkoxy group having 1 to 6 carbon atoms, a halogen atom and an oxo group, such as 1-oxo-1,2,3,4-tetrahydroisoquinolinyl, 2-oxopiperidinyl, 2-oxo-1-azacycloheptyl, 2-oxopyrrolidinyl, 1,3-dioxoisoindolinyl, 2,4-dioxoimidazolidinyl, 2-oxooxazolidinyl, 1-methylimidazolyl, 1-propylimidazolyl, 4-methylimidazolyl, 5,6-dimethylbenzimidazolyl, 1,4-dimethylpyrrolyl, 2-isopropylimidazolyl, 4-methylpiperazinyl, 4-phenylpiperidinyl, 4-methylthiazolyl, 2-oxothiazolyl, 5-ethylthiazolyl, 4-phenylthiazolyl, 4-propylthiazolyl, 5-butylthiazolyl, 4-pentylthiazolyl, 2-hexylthiazolyl, 3,5-dimethylisooxazolyl, 4,5-dimethylthiazolyl, 5-methoxy-4-methylthiazolyl, 1-ethylimidazolyl, 4-propylimidazolyl, 5-butylimidazolyl, 1-pentylimidazolyl, 1-hexylimidazolyl, 1,4-dimethylimidazolyl, 1,4,5-trimethylimidazolyl, 1-methyoxyimidazolyl, 2-ethoxyimidazolyl, 5-propoxyimidazolyl, 1-methyl-4-chloroimidazolyl, 4,5-dichloroimidazolyl, 3-methyl-1,2,4-triazolyl, 5-ethyl-1,2,4-triazolyl, 3-methyl-1,2,4-triazolyl, 2-oxo-1-methylimidazolyl, 2-oxoimidazolyl, 2-ethylpyrrolyl, 3-propylpyrrolyl, 5-butylpyrrolyl, 4-pentylpyrrolyl, 2-hexylpyrrolyl, 2,4,5-trimethylpyrrolyl, 2-bromopyrrolyl, 2,5-dibromopyrrolyl, 2-methyl-5-methoxypyrrolyl, 2-oxopyrrolyl, 1-methyl-1,2,3,4-tetrazolyl, 1-isopropyl-1,2,3,4-tetrazolyl, 1-ethyl-1,2,3,4-tetrazolyl, 1-propyl-1,2,3,4-tetrazolyl, 1-butyl-1,2,3,4-tetrazolyl, 1-pentyl-1,2,3,4-tetrazolyl, 1-hexyl-1,2,3,4-tetrazolyl, 5-methoxyindolyl, 2-methylpyridyl, 3-ethylpyridyl, 4-propylpyridyl, 2-butylpyridyl, 3-pentylpyridyl, 4-hexylpyridyl, 2-methoxypyridyl, 3-phenylpyridyl, 4-phenylpyridyl, 2,4-dimethylpyridyl, 2,4,6-trimethylpyridyl, 2-methyl-4- chloropyridyl, 2,4-difluoropyridyl, 2,4,6-trichloropyridyl, 2-oxopyridyl, 4-oxopyridyl, 4-methyl-2-oxopyridyl, 2-chloro-4-oxopyridyl, 3-methylimidazo-[1,2-a]pyridyl, 4-ethylimidazo[1,2-a]pyridyl, 3-methoxyimidazo-[1,2-a] pyridyl, 5-chloroimidazo[1,2-a]pyridyl, 3-methyl-1H-indazolyl, 3-iodo-1H-indazolyl, 1-methyl-1,2,3,4-tetrahydroisoquinolinyl, 5-ethyl-1,2,3,4-tetrahydroisoquinolinyl, 6-bromo-1,2,3,4-tetrahydroisoquinolinyl, 1-oxo-6-methyl-1,2,3,4-tetrahydroisoquinolinyl, 1-oxo-7-methoxy-1,2,3,4-tetrahydroisoquinolinyl, 3,4-dimethylpiprazinyl, 3-ethylpyrrolidinyl, 2-propylpyrrolidinyl, 1-methylpyrrolidinyl, 3,4,5-trimethylpiperidinyl, 4-butylpiperidinyl, 3-pentylmorpholino, 4-hexylpiperazinyl, 3-methylthiomorpholino, 3-chloropyrrolidinyl, 2-oxo-4-methylpiperidinyl, 2-oxo-3-methylpyrrolidinyl, 2-oxo-4-fluoropiperidinyl, 4-methyl-1-azacycloheptyl, 5-methoxy-1-azacycloheptyl, 6-methyl-2-oxo-1-azacycloheptyl, 1-methyl-2-oxoimidazolidinyl, 1-isobutyl-2-oxoimidazolidinyl, 1-methyl-2-oxoimidazolidinyl, 2-oxotetrahydro-1,3-oxazinyl, 3-bromo-2-oxo-1-azacycloheptyl, 2-oxo-tetrahydrooxazolyl, 3-chloropyridyl, 4-methylpiperazinyl, 4-isobutylpiperazinyl, 4-methylhomopiperazinyl, 3-chloropiperazinyl, 4-methoxypiperazinyl and 4-ethylhomopierazinyl groups can be exemplified.

As to the lower alkoxy group, a straight- or branched-chain alkoxy group having 1 to 6 carbon atoms, such as a methoxy, ethoxy, propoxy, isopropoxy, butoxy, tert-butoxy, pentyloxy and hexyloxy groups can be exemplified.

As to the lower alkyl group, a straight- or branched-chain alkyl group having 1 to 6 carbon atoms, such as a methyl, ethyl, propyl, isopropyl, butyl, isobutyl, tert-butyl, pentyl and hexyl groups can be exemplified.

As to the cycloalkyl group, a cycloalkyl group having 3 to 8 carbon atoms, such as cyclopropyl, cyclobutyl, cyclopentyl, cyclohexyl, cycloheptyl and cyclooctyl groups can be exemplified.

As to the isooxazolylcarbonyl group which may have 1 to 3 lower alkyl groups as the substituents, an isooxazolylcarbonyl group which may have 1 to 3 straight- or branched-chain alkyl groups having 1 to 6 carbon atoms as the substituents, such as isooxazolylcarbonyl, 3,5-dimethylisooxazolylcarbonyl, 3-methylisoxazolylcarbonyl, 4-ethylisooxazolylcarbonyl, 5-propylisooxazolylcarbonyl, 3-butylisooxazolylcarbonyl, 4-pentylisooxazolylcarbonyl, 5-hexylisooxazolylcarbonyl and 3,4,5-trimethylisooxazolylcarbonyl groups can be exemplified.

As to the amino-substituted lower alkyl group which may have lower alkyl groups as the substituents, an amino-substituted straight- or branched-chain alkyl group having 1 to 6 carbon atoms, which may have 1 to 2 straight- or branched-chain alkyl group having 1 to 6 carbon atoms as the substituents, such as an aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, 2-diethylaminoethyl, 2-dimethylaminoethyl, (N-ethyl-N-propylamino)methyl and 2-(N-methyl-N-hexylamino)ethyl groups can be exemplified.

As to the 5- to 6-membered saturated heterocyclic group formed by combining $R^5$ and $R^6$ together with the adjacent nitrogen atom being bonded thereto, further with or without other nitrogen atom or oxygen atom, such as pyrrolidinyl, piperidinyl, piperazinyl and morpholino groups can be exemplified.

As to the said heterocyclic group having 1 to 3 substituents selected from the group consisting of a hydroxyl group and a phenyl group, such as 4-phenyl-4-hydroxypiperidinyl, 4-phenylpiperazinyl, 3-phenylpiperazinyl, 3-hydroxypyrrolidinyl, 4-hydroxypiperazinyl, 3-phenylmorpholino, 2,4-diphenylpiperazinyl, 3-phenylpyrrolidinyl, 2,3,4-triphenylpiperazinyl, 3-hydroxymorpholino, 2-phenyl-2-hydroxymorpholino and 3-phenyl-3-hydroxypiperazinyl groups can be exemplified.

As to the lower alkenyl group, a straight- or branched-chain alkenyl group having 2 to 6 carbon atoms, such as a vinyl, allyl, 2-butenyl, 3-butenyl, 1-methylallyl, 2-pentenyl and 2-hexenyl groups can be exemplified.

As to the lower alkoxycarbonyl group, a straight- or branched-chain alkoxycarbonyl group having 1 to 6 carbon atoms, such as methoxycarbonyl, ethoxycarbonyl, propoxycarbonyl, isopropoxycarbonyl, butoxycarbonyl, tert-butoxycarbonyl, pentyloxycarbonyl and hexyloxycarbonyl groups can be exemplified.

As to the phenoxy-lower alkyl group which may have cyano groups as the substituents on the phenyl ring, a phenoxy group-substituted straight- or branched-chain alkyl group having 1 to 6 carbon atoms, which may have 1 to 3 cyano groups as the substituents on the phenyl ring, such as a phenoxymethyl, 2-phenoxyethyl, 1-phenoxyethyl, 4-phenoxybutyl, 5-phenoxypentyl, 6-phenoxyhexyl, 1,1-dimethyl-2-phenoxyethyl, 2-methyl-3-phenoxypropyl, (2-cyanophenoxy)methyl, 2-(2-cyanophenoxy)ethyl, 3-phenoxypropyl, 4-(3-cyanophenoxy)-butyl, 5-(2-cyanophenoxy)pentyl, 6-(3-cyanophenoxy)-hexyl, (4-cyanophenoxy)methyl, 3-(2-cyanophenoxy)-propyl, 3-(3-cyanophenoxy)propyl, 1-(3-cyanophenoxy)-ethyl, 3-(3,4-dicyanophenoxy)propyl and 2-(3,4,5-tricyanophenoxy)ethyl groups can be exemplified.

As to the halogen atom-substituted lower alkyl group, a straight- or branched-chain alkyl group having 1 to 6 carbon atoms, having 1 to 3 halogen atoms as the substituents, such as trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-bromopropyl, 3-chloropropyl, 2,3-dichloropropyl, 4,4,4-trichlorobutyl, 4-fluorobutyl, 5-chloropentyl, 3-chloro-2-methylpropyl, 5-bromohexyl and 5,6-dichlorohexyl groups can be exemplified.

As to the lower alkoxycarbonyl group-substituted lower alkyl group, a straight- or branched-chain alkoxycarbonylalkyl group in which the alkyl group is a straight- or branched-chain alkyl group having 1 to 6 carbon atoms, and the alkoxy-carbonyl moiety is a straight- or branched-chain alkoxycarbonyl group having 1 to 6 carbon atoms, such as methoxycarbonylmethyl, 3-methoxycarbonylpropyl, ethoxycarbonylmethyl, 3-ethoxycarbonylpropyl, 4-ethoxycarbonylbutyl, 5-isopropoxycarbonylpentyl, 6-propoxycarbonylhexyl, 1,1-dimethyl-2-butoxycarbonylethyl, 2-methyl-3-tert-butoxycarbonylpropyl, 2-pentyloxycarbonylethyl and hexyloxycarbonylmethyl groups can be exemplified.

DETAILED DESCRIPTION OF THE PREFERRED EMBODIMENTS

The benzimidazole derivatives of the present invention can be prepared by various methods, for example they can be prepared by the methods of Reaction formula-1 through Reaction formula-4 as follows.

Reaction Formula-1

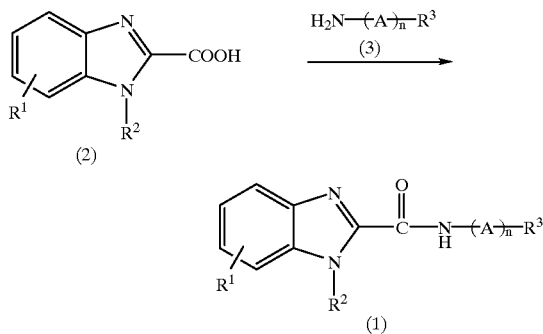

[wherein $R^1$, $R^2$, $R^3$, A and n are the same as defined above.]

The method as shown in Reaction formula-1 is the reaction of a benzimidazole compound (a carboxylic acid) of the formula (2) with an amine of the formula (3) by a common amide bond formation reaction. The acid amide bond formation reaction can easily be carried out by the reaction conditions of amide bond formation known in the art. For example, (a) a mixed-acid anhydrides method: i.e., a method by reacting a carboxylic acid (2) with an ester of alkylhalocarboxylate to form a mixed-acid anhydride, then by reacting it with an amine (3); (b) an activated ester method: i.e., a method by changing a carboxylic acid (2) to an activated ester form, e.g., p-nitrophenyl ester, N-hydroxysuccinimide ester, 1-hydoxybenztriazole ester, or the like, then by reacting the activated ester with an amine (3); (c) a carbodiimide method: i.e., a method by reacting a carboxylic acid (2) with an amine (3) in the presence of an activating agent, e.g., dicyclohexylcarbodiimide, carbonyldiimidazole or the like; (d) other method; for example, a method by changing a carboxylic acid (2) with a dehydrating agent, e.g., acetic anhydride to form carboxylic acid anhydride, then by reacting said acid anhydride with an amine (3); a method by reacting an ester of a carboxylic acid (2) and a lower alcohol, with an amine (3) at an elevated temperature; a method by reacting a acid halogenide of a carboxylic acid (2), e.g., a carboxylic acid halide, with an amine (3), and the like can be exemplified.

The mixed acid anhydride, which is used in the above-mentioned a mixed-acid anhydrides method, can be prepared by a method similar to that employed in common Schotten-Baumann reaction, said mixed-acid anhydride is used without being isolated from the reaction system, and reacted with an amine (3) to obtain a benzimidazole compound of the general formula (1) of the present invention. The above-mentioned Schotten-Baumann reaction is carried out in the presence of a basic compound. As to the basic compound to be used in the reaction, usual basic compounds used in Schotten-Baumann reaction, for example organic bases such as triethylamine, trimethylamine, pyridine, dimethylaniline, 1-methyl-2-pyrrolidinone (NMP), N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO) and the like, and inorganic bases such as potassium carbonate, sodium carbonate, potassium hydrogencarbonate, sodium hydrogencarbonate and the like can be exemplified. Said reaction is generally carried out at about −20 to 100° C., preferably at about 0 to 50° C., and the reaction time is about 5 minutes to 10 hours, preferably about 5 minutes to 2 hours. The reaction of the thus obtained mixed acid anhydride with an amine (3) is carried out at about −20 to 150° C., preferably at about 10 to 50° C., and the reaction time is about 5 minutes to 10 hours, preferably about 5 minutes to 5 hours. Generally, the mixed-acid anhydride method is carried out in a solvent. As to the solvent to be used for the reaction, any solvent commonly used for the mixed-acid anhydride method can be used, specifically halogenated hydrocarbons such as chloroform, dichloromethane and the like; aromatic hydrocarbons such as benzene, p-chlorobenzene, toluene, xylene and the like; ethers such as diethyl ether, diisopropyl ether, tetrahydrofuran, dimethoxyethane and the like; esters such as methyl acetate, ethyl acetate and the like; aprotic polar solvents such as N,N-dimethylformamide, dimethyl sulfoxide, acetonitrile, hexamethylphosphoric triamide and the like; and mixed solvents thereof can be exemplified. As to the alkylhalocarbonic acid ester used in the mixed-acid anhydride method, methyl chloroformate, methyl bromoformate, ethyl chloroformate, ethyl bromoformate, isobutyl chloroformate and the like can be exemplified. Ratio of the amounts of a carboxylic acid (2), an alkylhalocarboxylic acid ester and an amine (3) used in said method may be equimolar quantities, respectively, and within the range of about 1 to 1.5 times the molar quantities of the alkylhalocarboxylic acid ester and the carboxylic acid (2), respectively, can be used to 1 molar quantity of the amine (3).

Among the methods (d), in case of using the method by reacting carboxylic acid halide with an amine (3), said reaction can be carried out, in the presence of a basic compound, in a suitable solvent. As to the basic compound to be used, known compound selected from a wide range can be used, for example in addition to the basic compounds used in the Schotten-Baumann reaction, sodium hydroxide, potassium hydroxide, sodium hydride, potassium hydride and the like can be exemplified. As to the solvent to be used in the reaction, for example in addition to the solvents used in the above-mentioned mixed acid anhydride method, alcohols such as methanol, ethanol, propanol, butanol 3-methoxy-1-butanol, ethyl cellosolve, methyl cellosolve and the like; pyridine, acetone, water can be exemplified. Ratio of the amount of amine (3) and to the amount of carboxylic acid halide is not specifically restricted and can be suitably selected from a wide range, generally, at least about an equimolar quantity, preferably about an equimolar to 5 times the molar quantity of the latter may be used to the former. Generally, said reaction is carried out at about −20 to 180° C., preferably at about 0 to 150° C., and generally, the reaction is completed within for about 5 minute to 30 hours.

Furthermore, the amide bond formation reaction shown in the above-mentioned Reaction formula-1 can also be carried out by reacting a carboxylic acid (2) with an amine (3), in the presence of a phosphorus compound as a condensing agent, such as phenylphosphin-2,2'-dithiopyridine, diphenylphosphinyl chloride, phenyl-N-phenylphosphoramide chloridate, diethylchlorophosphate, diethyl cyanophosphate, diphenylphosphoric acid azide or bis(2-oxo-3-oxazolidinyl) phosphinic chloride, as a condensing agent.

Said reaction is carried out, in the presence of the solvent and the basic compound used in the reaction of the above-mentioned carboxylic acid halide with an amine (3) generally at about −20 to 150° C., preferably at about 0 to 100° C., and the reaction is generally completed within about 5 minute to 30 hours. The amounts of the condensing agent and the carboxylic acid (2) may be about equimolar quantity, preferably about equimolar to 2 times the molar quantity, respectively to the amount of the amine (3).

The reaction as shown in Reaction formula-1 can also be carried out by reacting an ester of carboxylic acid (2) and a lower alcohol with an amine (3) in a solvent or without solvent, and in the presence or absence of a basic compound. Generally, the reaction is carried out at about room temperature to 200° C., preferably at about room temperature to 120° C. and generally, the reaction is completed within 30 minutes to 5 hours. The amine (3) is used in an amount at least 0.5 times the molar quantity, preferably 0.5 to 3 times the molar quantity to an equimolar quantity of the ester of carboxylic acid (2) and a lower alcohol. As to the solvent to be used in this reaction, any solvent used in the above-mentioned reaction of a carboxylic acid halide with an amine (3) can also be used. As to the basic compound to be used in this reaction, in addition to the basic compounds used in the above-mentioned method for reacting an carboxylic acid halide with an amine (3), for example an alkali metal alcoholate, such as sodium methylate, sodium ethylate, potassium methylate, potassium ethylate or the like can be exemplified.

The reaction as shown in Reaction formula-1 can also be carried out by reacting, in a suitable solvent, an aluminum compound such as lithium aluminum hydride, trimethyl aluminum and the like as a condensing agent with an amine (3), then reacting the resulting reaction product with an ester of carboxylic acid (2) and a lower alcohol. As to the solvent used in this reaction, ethers such as dioxane, diethyl ether, diglyme, tetrahydrofuran and the like; aromatic hydrocarbons such as benzene, toluene, xylene and the like; aliphatic hydrocarbons such as cyclohexane, heptane, hexane and the like; and the mixtures of these solvents can be exemplified. The amine (3) may be used at least in an equimolar quantity, preferably in an equimolar to 5 times the molar quantity of the ester of the carboxylic acid (2) and lower alcohol. The condensing agent may be used at least in an equimolar quantity, preferably in an equimolar to 1.5 times the molar quantity of the ester of the carboxylic acid (2) and lower alcohol. The reaction of the condensing agent with the amine (3) is generally carried out at about −80 to 100° C., and the reaction is generally completed within for about 30 minutes to 20 hours. The subsequent ester reaction of the carboxylic acid (2) with the lower alcohol is carried out generally at room temperature to 200° C., preferably at about room temperature to 150° C., and the reaction is generally completed within 1 to 10 hours.

Reaction Formula-2

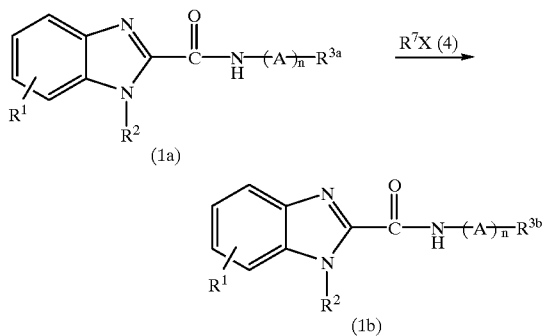

[wherein $R^1$, $R^2$, A and n are the same as defined above;
$R^{3a}$ is a heterocyclic group as defined in $R^3$ which may have 1 to 2 substituents selected from the group consisting of:
a group of the formula —B—$R^4$ (B and $R^4$ are the same as defined above); a lower alkenyl group; a lower alkoxycarbonyl group; a phenoxy-lower alkyl group which may have cyano groups as the substituents in the phenyl ring; a halogen substituted-lower alkyl group; and a lower alkoxycarbonyl substituted-lower alkyl group;
further $R^{3a}$ is a heterocyclic group as defined in $R^3$, having a group of the formula —NH— in said heterocyclic group:
$R^{3b}$ is a heterocyclic group as defined in $R^3$ which may have 1 to 2 substituents selected from the group consisting of:
a group of the formula —B—$R^4$ (B and $R^4$ are the same as defined above); a lower alkenyl group; a lower alkoxycarbonyl group; a phenoxy-lower alkyl group which may have cyano groups as the substituents in the phenyl ring; a halogen substituted-lower alkyl group; and a lower alkoxycarbonyl substituted-lower alkyl group;
further $R^{3b}$ is a heterocyclic group as defined in $R^3$, having a group of the formula —N($R^7$)— ($R^7$ is a group of the formula —B—$R^4$ (wherein B and $R^4$ are the same as defined above); a lower alkenyl group, a lower alkoxycarbonyl group; a phenoxy-lower alkyl group which may have cyano groups as the substituents in the phenyl ring; a halogen substituted-lower alkyl group; or a lower alkoxycarbonyl substituted-lower alkyl group) in said heterocyclic group; X is a halogen atom, a lower alkanesulfonyloxy group, an arylsulfonyoxy group or an aralkylsulfonyloxy group].

As to the lower alkanesulfonyloxy group, specifically methanesulfonyloxy, ethanesulfonyloxy, propanesulfonyloxy, isopropanesulfonyloxy, butanesulfonyloxy, tert-butanesulfonyloxy, pentanesulfonyloxy and hexanesulfonyloxy groups and the like can be exemplified. As to the arylsulfonyloxy group, specifically substituted or unsubstituted arylsulfonyloxy groups such as phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy and α-naphthylsulfonyloxy groups and the like can be exemplified.

As to the aralkylsulfonyloxy group, specifically substituted or unsubstituted aralkylsulfonyloxy groups such as benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy and α-naphthylmethylsulfonyloxy groups can be exemplified.

The reaction of a compound (1a) with a compound (4) is carried out, generally in a suitable inert solvent, in the presence or absence of a basic substances. As to the inert solvent, for example aromatic hydrocarbons such as benzene, toluene, xylene and the like; ethers such as tetrahydrofuran, dioxane, diethylene glycol dimethyl ether and the like; halogenated hydrocarbons such as dichloromethane, chloroform, carbon tetrachloride and the like; lower alcohols such as methanol, ethanol, isopropanol, butanol, tert-butanol and the like; acetic acid, ethyl acetate, acetone, acetonitrile, pyridine, dimethyl sulfoxide, dimethylformamide, hexamethylphosphoric triamide; and mixtures of these solvents can be exemplified. As to the basic substances, carbonates such as sodium carbonate, potassium carbonate, sodium hydrogencarbonate, potassium hydrogencarbonate and the like; metal hydroxide such as sodium hydroxide, potassium hydroxide and the like; sodium hydride, potassium metal, sodium metal, sodium amide; metal alcoholates such as sodium methylate, sodium ethylate and the like; organic bases such as pyridine, N-ethyldiisopropylamine, dimethylaminopyridine, triethylamine, 1,5-diazabicyclo[4.3.0]nonene-5 (DBN), 1,8-diazabicyclo-[5.4.0]undecene-7 [DBU], 1,4-diazabicyclo [2.2.2]octane (DABCO) and the like can be exemplified. Ratio of the amounts of compound (1a) and compound (4) is not specifically restricted and can be selected from a wide range, generally at least about an equimolar quantity, preferably about an equimolar to 10 times the molar quantities of the latter may be used to the former. The reaction is generally carried out at about 0 to 200° C., preferably at about 0 to 170° C., and generally, the reaction is completed within 30 minutes to 75 hours. Alkali metal halogenides such as sodium iodide, potassium iodide; or copper metal powder may be added to the reaction system.

Reaction Formula-3

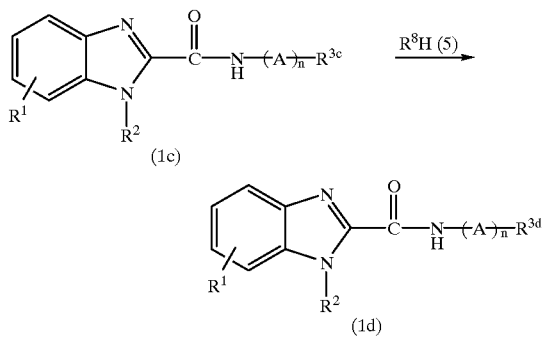

[wherein $R^1$, $R^2$, A and n are the same as defined above;

$R^{3c}$ is a heterocyclic group as defined in $R^3$, which may have 1 to 2 substituents selected from the group consisting of:

a group of the formula —B—$R^4$, (B and $R^4$ are the same as defined above); a lower alkenyl group; a lower alkoxycarbonyl group; a phenoxy-lower alkyl group which may have cyano groups as the substituents in the phenyl ring; a halogen substituted-lower alkyl group; and a lower alkoxycarbonyl substituted-lower alkyl group;

further $R^{3c}$ is a heterocyclic group as defined in $R^3$, having a group of the formula —N($R^9$)— ($R^9$ is a halogen substituted-lower alkyl group) in said heterocyclic group;

$R^{3d}$ is a heterocyclic group as defined in $R^3$, which may have 1 to 2 substituents selected from the group consisting of:

a group of the formula —B—$R^4$ (B and $R^4$ are the same as defined above); a lower alkenyl group; a lower alkoxycarbonyl group; a phenoxy-lower alkyl group which may have cyano groups as the substituents in the phenyl ring; a halogen substituted-lower alkyl group; and a lower alkoxycarbonyl substituted-lower alkyl group;

further, $R^{3d}$ is a heterocyclic group as defined in $R^3$, having a group of the formula —N($R^{10}$)— ($R^{10}$ is a group of the formula —B—$R^4$ (B and $R^4$ are the same as defined above); or a phenoxy-lower alkyl group which may have cyano groups as the substituents in the phenyl ring) in said heterocyclic group;

$R^8$ is a group of the formula —$R^{4a}$ ($R^{4a}$ is a heterocyclic group as defined in $R^4$, having at least one group of the formula —N< in said heterocyclic group, or a group of the formula —N$R^5R^6$ ($R^5$ and $R^6$ are the same as defined above); or a phenoxy group which may have cyano groups as the substituents in the phenyl ring].

The reaction of a compound (1c) with a compound (5) is carried out under the reaction condition similar to the reaction condition of a compound (1a) with a compound (4) in the above-mentioned Reaction formula-2.

Reaction Formula-4

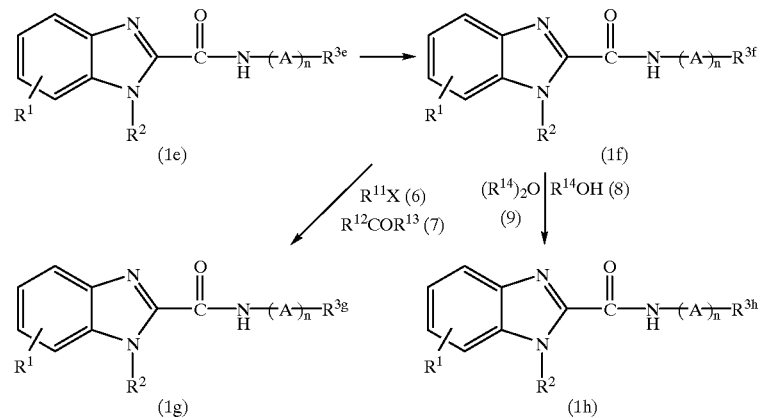

[wherein $R^1$, $R^2$, A and n are the same as defined above;

$R^{3e}$ is a heterocyclic group as defined in $R^3$, which may have 1 to 2 substituents selected from the group consisting of:

a group of the formula —B—$R^4$ (B and $R^4$ are the same as defined above); a lower alkenyl group; a lower alkoxycarbonyl group; a phenoxy-lower alkyl group which may have cyano groups as the substituents in the phenyl ring; a halogen substituted-lower alkyl group; and a lower alkoxycarbonyl substituted-lower alkyl group;

further $R^{3e}$ is a heterocyclic group as defined in $R^3$, having a group of the formula —N($R^{15}$)—, ($R^{15}$ is a phthalimide substituted-lower alkyl group) in said heterocyclic group;

$R^{3f}$ is a heterocyclic group as defined in $R^3$ which may have 1 to 2 substituents selected from the group consisting of:
   a group of the formula —B—$R^4$ (B and $R^4$ are the same as defined above); a lower alkenyl group; a lower alkoxycarbonyl group; a phenoxy-lower alkyl group which may have cyano groups as the substituents in the phenyl ring; a halogen substituted-lower alkyl group; and a lower alkoxycarbonyl substituted-lower alkyl group;
further $R^{3f}$ is a heterocyclic group as defined in $R^3$, having a group of the formula —N($R^{16}$)— ($R^{16}$ is an amino group-substituted lower alkyl group) in the heterocyclic ring;
$R^{3g}$ is a heterocyclic group as defined in $R^3$, which may have 1 to 2 substituents selected from the group consisting of:
   a group of the formula —B—$R^4$ (wherein B and $R^4$ are the same as defined above); a lower alkenyl group; a lower alkoxycarbonyl group; a phenoxy-lower alkyl group which may have cyano groups as the substituents in the phenyl ring; a halogen substituted-lower alkyl group; and a lower alkoxycarbonyl substituted-lower alkyl group;
further $R^{3g}$ is a heterocyclic group as defined in $R^3$, having a group of the formula —N(B-N$R^{5a}R^{11}$)— (B is the same as defined above; $R^{5a}$ is a hydrogen atom, a lower alkyl group, a cycloalkyl group, a pyridylcarbonyl group, an isoxazolylcarbonyl group which may have 1 to 3 lower alkyl groups as the substituents; a pyrrolycarbonyl group or an amino group substituted-lower alkyl group which may have lower alkyl groups as the substituents; $R^{11}$ is a lower alkyl group, a cycloalkyl group or an amino group substituted-lower alkyl group which may have lower alkyl groups as the substituents) in said heterocyclic group;
$R^{3h}$ is a heterocyclic group as defined in $R^3$, which may have 1 to 2 substituents selected from the group consisting of:
   a group of the formula —B—$R^4$ (B and $R^4$ are the same as defined above); a lower alkenyl group; a lower alkoxycarbonyl group; a phenoxy-lower alkyl group which may have cyano groups as the substituents in the phenyl ring; a halogen substituted-lower alkyl group; and a lower alkoxycarbonyl substituted-lower alkyl group;
further $R^{3h}$ is a heterocyclic group as defined in $R^3$, having a group of the formula —N(B—NR$^{5a}R^{14}$) (B and $R^{5a}$ are the same as defined above; and $R^{14}$ is a pyridylcarbonyl group, an isoxazolylcarbonyl group which may have 1 to 3 lower alkyl groups as the substituents, or a pyrrolylcarbonyl group) in said heterocyclic group;
$R^{12}$ and $R^{13}$ are each, a hydrogen atom or a lower alkyl group, respectively].

The reaction for introducing a compound (1f) from a compound (1e) can be carried out by reacting a compound (1e) with hydrazine in a suitable solvent or by hydrolysis of a compound (1e). As to the solvent to be used in the reaction of a compound (1e) with hydrazine, in addition to water, solvents similar to those can be used in the reaction of a compound (1a) with a compound (4) in the above-mentioned Reaction formula-2 can be used. This reaction is carried out generally at about room temperature to 120° C., preferably at about 0 to 100° C., and the reaction is generally completed within 0.5 to 15 hours. The amount of hydrazine is at least about an equimolar quantity, preferably an equimolar to 5 times the molar quantities can be used to a compound (1e).

The above-mentioned hydrolysis reaction of a compound (1e) can be carried out in a suitable solvent or without solvent, in the presence of an acid or basic compound. As to the solvent to be used, water, lower alcohols such as methanol, ethanol, isopropanol and the like; ketones such as acetone, methyl ethyl ketone and the like; ethers such as dioxane, tetrahydrofuran, ethylene glycol dimethyl ether and the like; fatty acids such as acetic acid, formic acid and the like; and mixtures of these solvents can be exemplified. As to the acid to be used, mineral acids such as hydrochloric acid, sulfuric acid, hydrobromic acid and the like; organic acid such as formic acid, acetic acid, aromatic sulfonic acid such as p-toluenesulfonic acid and the like can be exemplified. As to the basic compound to be used, metal carbonates such as sodium carbonate, potassium carbonate and the like, metal hydroxides such as sodium hydroxide, potassium hydroxide, calcium hydroxide, lithium hydroxide and the like can be exemplified. Generally, said reaction is suitably carried out at about room temperature to 200° C., preferably at about room temperature to 150° C., and generally the reaction is completed within about 10 minutes to 25 hours.

The reaction of a compound (1f) with a compound (8) is carried out under the reaction condition similar to that of employed in the reaction of a compound (2) with a compound (3) in the above-mentioned Reaction formula-1.

The reaction of a compound (1f) with a compound (6) is carried out, generally in a suitable inert solvent, in the presence or absence of a basic substance. As to the inert solvent to be used in the reaction, aromatic hydrocarbons such as benzene, toluene, xylene and the like; ethers such as tetrahydrofuran, dioxane, diethylene glycol dimethyl ether and the like; halogenated hydrocarbons such as dichloromethane, chloroform, carbon tetrachloride and the like; lower alcohols such as methanol, ethanol, isopropanol, butanol, tert-butanol and the like; acetic acid, ethyl acetate, acetone, acetonitrile, pyridine, dimethyl sulfoxide, dimethyl formamide, hexamethylphosphoric triamide; or mixtures of these solvents can be exemplified. As to the basic substances to be used in the reaction, carbonates such as sodium carbonate, potassium carbonate, sodium hydrogencarbonate, potassium hydrogencarbonate; metal hydroxides such as sodium hydroxide, potassium hydroxide; sodium hydride, potassium metal, sodium metal, sodium amide, metal alcoholates such as sodium methylate, sodium ethylate and the like; organic bases such as pyridine, N-ethyldiisopropylamine, dimethylaminopyridine, triethylamine, 1,5-diazabicyclo[4.3.0]nonene-5 (DBN), 1,8-diazabicyclo[5.4.0]undecene-7 (DBU), 1,4-diazabicyclo-[2.2.2]octane (DABCO) and the like can be exemplified. Ratio of the amounts of a compound (1f) to a compound (6) is not specifically restricted, and can be selected from a wide range, at least about an equimolar quantity, preferably an equimolar to 10 times the molar quantities of the latter may be used to the former. Said reaction is carried out generally, at about 0 to 200° C., preferably at about 0 to 170° C., and the reaction is completed within 30 minutes to 75 hours. Into the reaction system, an alkali metal halogenides such as sodium iodide, potassium iodide or the like, copper powder may be added.

The reaction of a compound (1f) with a compound (7) is carried out without solvent or in a suitable solvent, in the presence of a reducing agent. As to the solvent to be used in the reaction, water; alcohols such as methanol, ethanol, isopropanol and the like; acetonitrile; formic acid, acetic acid; ethers such as dioxane, diethyl ether, diglyme, tetrahydrofuran and the like; aromatic hydrocarbons such as benzene, toluene, xylene and the like; and mixtures of these solvents can be exemplified. As to the reducing agent, formic acid, ammonium formate, alkali metal salts of fatty acid such as sodium formate; hydride reducing agents such as sodium borohydride, sodium cyanoborohydride, lithium aluminum hydride and the like; catalytic hydrogenation reducing agents such as palladium-black, palladium-carbon, platinum oxide, platinum black, Raney nickel and the like can be exemplified.

In case of using formic acid as a reducing agent, reaction temperature is generally at about room temperature to 200° C., preferably at about 50 to 150° C. may be suitable, and the reaction is completed within about 1 to 10 hours. Formic acid may be used in a large excess amount against a compound (1f).

In case of using hydride reducing agent, reaction temperature is generally at about −30 to 100° C., preferably at about 0 to 70° C. may be suitable, and the reaction is completed for about 30 minutes to 12 hours. Reducing agent may be used generally in about an equimolar to 20 times the molar quantities, preferably about 1 to 6 times the molar quantities to a compound (1f). Particularly, in case of using lithium aluminum hydride as the reducing agent, preferably ethers such as diethyl ether, dioxane, tetrahydrofuran, diglyme and the like; aromatic hydrocarbons such as benzene, toluene, xylene and the like may be used.

Furthermore, in case of using a catalytic hydrogenation reducing agent, the reduction is carried out in hydrogen gas atmosphere under about normal pressure to 20 atmospheric pressure, preferably about normal pressure to 10 atmospheric pressure, on the other hand in case of using reduction in the presence of a hydrogen donating agent such as formic acid, ammonium formate, cyclohexene, hydrazine hydrate or the like, the reducing reaction may be carried out at about −30 to 100° C., preferably at about 0 to 60° C., and generally the reaction is completed within 1 to 12 hours. The catalytic hydrogenation reducing agent may be used generally in an amount of 0.1 to 40% by weight, preferably 1 to 20% by weight to compound (1f). The hydrogen donating agent may be used in an amount of a large excess quantity to compound (1f).

Compound (7) may be used, generally at least in an equimolar quantity, preferably an equimolar to a large excess quantity to compound (1f).

The reaction of compound (1f) with compound (9) is carried out without solvent or in a suitable solvent, in the presence or absence of a basic compound. As to the suitable solvent, for example aromatic hydrocarbons as previously mentioned; lower alcohols such as methanol, ethanol, propanol and the like; dimethylformamide, dimethyl sulfoxide and the like; halogenated hydrocarbons such as chloroform, methylene chloride and the like; acetone, pyridine and the like can be used. As to the basic compound for example, organic bases such as triethylamine, pyridine, sodium hydroxide, potassium hydroxide, sodium hydride and the like can be exemplified. The above-mentioned reaction can also be carried out in a solvent, such as acetic acid, in the presence of a mineral acid such as sulfuric acid. Ratio of the amount of compound (9) may be used in an equimolar to a large excess quantity to the starting material, and the reaction is carried out generally at about 0 to 200° C., preferably at about 0 to 150° C., and the reaction is completed within 0.5 to 20 hours.

Compound (2) and compound (3) which are used for the starting materials are easily prepared by methods as shown in Reaction formula-5 through Reaction formula-9 as follows.

Reaction Formula-5

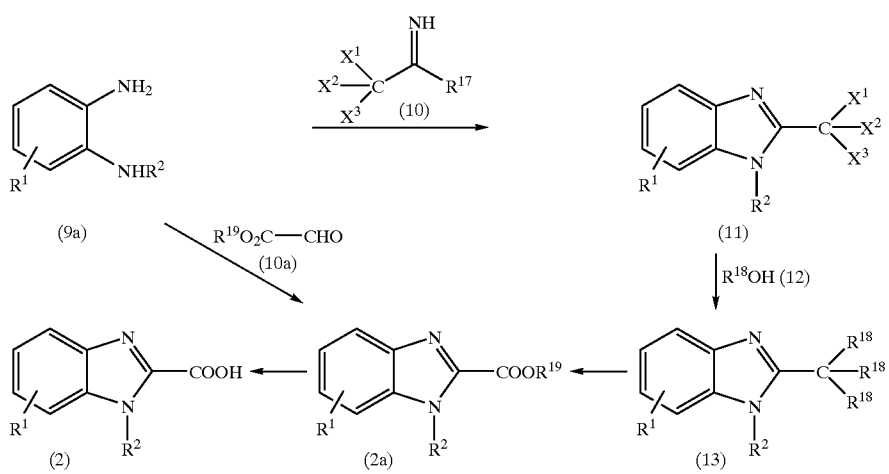

[wherein $R^1$ and $R^2$ are the same as defined above; $R^{17}$ is a lower alkoxy group; $R^{18}$ is a lower alkoxy group; $R^{19}$ is a lower alkyl group; $X^1$, $X^2$ and $X^3$ are each hydrogen atom, respectively].

The reaction of a compound (9a) with a compound (10) can be conducted in a suitable solvent in the presence of an acid. As to the solvent to be used in the reaction, for example water, lower alcohols such as methanol, ethanol, isopropanol and the like; ketones such as acetone, methyl ethyl ketone and the like; ethers such as dioxane, tetrahydrofuran, ethylene glycol dimethyl ether and the like; fatty acids such as acetic acid, formic acid and the like; mixtures of these solvents, can be mentioned. As to the acid to be used in the reaction, mineral acids such as hydrochloric acid, sulfuric acid, hydrobromic acid and the like; organic acids such as formic acid, acetic acid, aromatic sulfonic acids such as p-toluenesulfonic acid can be exemplified. A compound (10) may be used at least in an equimolar quantity, preferably an equimolar to 2 times the molar quantities to a compound (9a). Said reaction is carried out preferably at about room temperature to 200° C., desirably at about room temperature to 150° C., the reaction is generally completed within 0.5 to 5 hours.

The reaction of a compound (11) with a compound (12) is carried out under the reaction condition similar to that employed in the reaction of a compound (1a) with a compound (4) in the above-mentioned Reaction formula-2. In the case, a compound (12) may be used as a solvent in a large excess quantity.

The reaction for introducing a compound (13) to a compound (2a), and the reaction for introducing a compound (2a) to a compound (2) are carried out under the reaction condition similar to that employed in the hydrolysis for introducing a compound (1e) to a compound (1f) among the reactions shown in the abovementioned Reaction formula-4. The reaction of a compound (9a) with a compound (10a) is carried out under the reaction condition similar to that employed in the above-mentioned reaction of a compound (9a) with a compound (10), or is carried out in a suitable solvent, in the presence or absence of an acid, in the presence of an oxidizing agent. As to the solvent to be used therein, water; lower alcohol such as methanol, ethanol, isopropanol and the like; ethers such as dioxane, tetrahydrofuran, ethylene glycol dimethyl ether and the like; fatty acids such as acetic acid, formic acid and the like; n-hexane; aromatic hydrocarbons such as benzene, toluene and the like; and mixtures of these solvents can be exemplified. As to the oxidizing agent to be used therein, iodine, nitro compounds such as nitrobenzene; dehydrogenating catalysts such as palladium-carbon, can be exemplified.

A compound (10a) may be used generally at least in an equimolar quantity, preferably in an equimolar to 3 times the molar quantities to a compound (9a). An oxidizing agent may be used generally in 0.1 times the molar quantity or more, preferably 0.1 to 2 times the molar quantities. The reaction is completed within for about 10 minutes to 5 hours. The reaction temperature and the acid to be used are similar to the reaction conditions employed in the above-mentioned reaction of a compound (9a) with a compound (10). In said reaction, when an oxidizing agent is added, then the desired compound (2a) of high purity can be obtained in high yield.

Reaction Formula-6

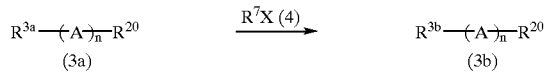

[wherein $R^{3a}$, $R^{3b}$, A, n, $R^7$ and X are the same as defined above; $R^{20}$ is an amino group or a group capable to convert into an amino group].

As to a group of $R^{20}$ capable to convert into an amino group, groups which can be converted into an amino group by conventional method, e.g., reduction, hydrolysis or the like, such as a nitro group, a cyano group, an azide group, a phthalimide group, can be exemplified.

The reaction of a compound (3a) with a compound (4) is carried out under the reaction condition similar to that employed in the reaction of a compound (1a) with a compound (4) in the above-mentioned Reaction formula-2.

Reaction Formula-7

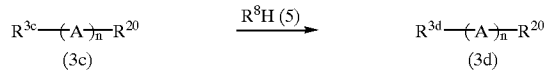

[wherein $R^{3c}$, $R^{3d}$, A, n, $R^{20}$ and $R^8$ are the same as defined above.].

The reaction of a compound (3c) with a compound (5) is carried out under the reaction condition similar to that employed in the reaction of a compound (1c) with a compound (5) in the above-mentioned Reaction formula-3.

Reaction Formula-8

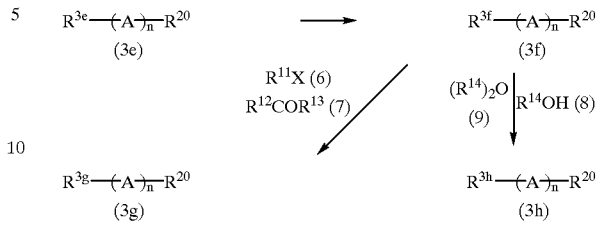

[wherein $R^{3e}$, A, n, $R^{20}$, $R^{3f}$, $R^{3g}$, $R^{3h}$, $R^{11}$, $R^{12}$, $R^{13}$, $R^{14}$ and X are the same as defined above].

The reaction for introducing a compound (3e) to a compound (3f) is carried out under the reaction condition similar to that employed in the reaction of a compound (1e) with a compound (1f) in the above-mentioned Reaction formula-4.

The reaction of a compound (3f) with a compound (6) or a compound (7) is carried out under the reaction condition similar to that employed in the reaction of a compound (1f) with a compound (6) or a compound (7) in the above-mentioned Reaction formula-4.

The reaction of a compound (3f) with a compound (8) or a compound (9) is carried out under the reaction condition similar to that employed in the reaction of a compound (1f) with a compound (8) or a compound (9) in the above-mentioned Reaction formula-4.

Each one of compounds (3a), (3b), (3c), (3d), (3e), (3f), (3g) and (3h) wherein $R^{20}$ is nitro group, can be introduced to each one of the corresponding compounds (3a), (3b), (3c), (3d), (3e), (3f), (3g) and (3h) wherein $R^{20}$ is amino group by reducing reaction. Said reducing reaction is carried out for example (i) by reducing each one of the former compounds in a suitable solvent by using a hydrogenation catalyst or (ii) by reducing each one of the former compounds in a suitable inert solvent, by using a chemical reducing agent such as a mixture of a metal or metal salt with an acid; or a metal or metal salt with an alkali metal hydroxide, sulfide, ammonium salt; or a hydride reducing agent such as lithium aluminum hydride.

In case of conducting the above-mentioned method of (i) by using the hydrogenation catalyst, as to the solvents for example, water, acetic acid, alcohols such as methanol, ethanol, isopropanol and the like; hydrocarbons such as hexane, cyclohexane and the like; ethers such as dioxane, tetrahydrofuran, diethyl ether, diethylene glycol dimethyl ether and the like; esters such as ethyl acetate, methyl acetate and the like; aprotic polar solvents such as N,N-dimethylformamide and the like; and mixtures of these solvents can be exemplified. As to the catalyst to be used for catalytic hydrogenation, palladium, palladium-black, palladium-carbon, platinum, platinum oxide, copper chromite, Raney nickel and the like can be exemplified. The catalyst may be used generally, in an amount of 0.02 to an equivalent quantity to the starting material. The reaction is carried out generally at about −20 to 150° C., preferably at about 0 to 100° C., and under 1 to 10 atmospheric pressure of hydrogen gas, and the reaction is completed generally within 0.5 to 10 hours. Further, an acid such as hydrochloric acid may be added to the reaction system.

In case of conducting method of (ii) as above, a mixture of iron, zinc, tin or stannous chloride with a mineral acid such as hydrochloric acid or sulfuric acid; or iron, ferrous sulfate, zinc or tin with an alkali metal hydroxide such as sodium hydroxide, a sulfide such as ammonium sulfide, ammonia water, an ammonium salt such as ammonium chloride; or a hydride reducing agent such as lithium aluminum hydride may be used as a reducing agent. As to the inert solvent to be used in the reaction, water, acetic acid, methanol, ethanol, dioxane or the like may be exemplified. In case of using lithium aluminum hydride as the reducing agent, ethers such as diethyl ether, dioxane, tetrahydrofuran, diglyme and the like may preferably be used as the solvent. The condition of the above-mentioned reducing reaction may be suitably selected in accordance with the reducing agent to be used, for example, in case of using a mixture of stannous chloride with hydrochloric acid as the reducing agent, the reaction may be carried out advantageously at about 0 to 80° C., and for about 0.5 to 10 hours. The reducing agent is used at least in an equimolar quantity, generally in an equimolar to 5 times the molar quantities to the starting compound.

Each one of compounds (3a), (3b), (3c), (3d), (3e), (3f), (3g) and (3h), wherein $R^{20}$ is nitrile group can be introduced to each one of the corresponding compounds (3a), (3b), (3c), (3d), (3e), (3f), (3g) and (3h), wherein $R^{20}$ is amino group by reducing reaction. For this reducing reaction, a hydride reducing agent is preferably used. As to the hydride reducing agent, lithium aluminum hydride, lithium borohydride, sodium borohydride, diborane and the like can be exemplified. The reducing agent is used at least in an equimolar quantity, preferably in the range of an equimolar to 15 times the molar quantities to the starting compound. Said reducing reaction is carried out in a suitable solvent, for example water; lower alcohols such as methanol, ethanol, isopropanol and the like; ethers such as tetrahydrofuran, diethyl ether, diisopropyl ether, diglyme and the like; and mixtures of these solvents, and generally at about –60 to 150° C., preferably –30 to 100° C., and for about 10 minutes to 15 hours. In case of using lithium aluminum hydride or diborane as the reducing agent, anhydrous solvents such as tetrahydrofuran, diethyl ether, diisopropyl ether, diglyme and the like can be used as the solvent. Further, in case of using sodium borohydride as the reducing agent, the reaction is advantageously proceeded by adding a metal halide such as cobalt chloride or the like to the reaction system.

Each one of compounds (3a), (3b), (3c), (3d), (3e), (3f), (3g) and (3h), wherein $R^{20}$ is a phthalimido group can be introduced to each one of the corresponding compounds (3a), (3b), (3c), (3d), (3e), (3f), (3g) and (3h), wherein $R^{20}$ is an amino group by treating under the reaction condition similar to that of employed in the reaction for introducing compound (1e) to compound (1f) in the above-mentioned Reaction formula-4.

Each one of compounds (3a), (3b), (3c), (3d), (3e), (3f), (3g) and (3h), wherein $R^{20}$ is an azido group can be introduced to each one of the corresponding compounds (3a), (3b), (3c), (3d), (3e), (3f), (3g) and (3h), wherein $R^{20}$ is an amino group by treating under the condition similar to those employed in the above-mentioned reduction of nitro group by using a catalytic hydrogenation or reduction of nitrile group by using a hydride reducing agent.

Reaction Formula-9

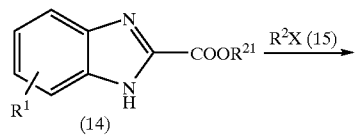

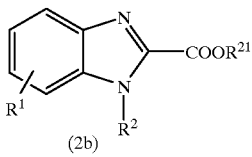

[wherein $R^1$, $R^2$ and X are the same as defined above; $R^{21}$ is a hydrogen atom or a lower alkyl group].

The reaction of a compound (14) with a compound (15) is carried out under the reaction condition similar to that employed in the reaction of a compound (1a) with a compound (4) as shown in the above-mentioned Reaction formula-2.

A compound represented by the general formula (1), wherein $R^3$ is a substituted or unsubstituted 2(1H)-quinolinonyl group can be introduced to the corresponding compound wherein $R^3$ is a substituted or unsubstituted 3,4-dihydro-2(H)-quinolinonyl group when the former is subjected to reducing reaction.

A compound represented by the general formula (1), wherein $R^3$ is a substituted or unsubstituted 3,4-dihydro-2(1H)-quinolinonyl group can be introduced to the corresponding compound wherein $R^3$ is a substituted or unsubstituted 2(1H)-quinolinonyl group when the former is subjected to dehydrogenation reaction.

In carrying out the above-mentioned reducing reaction, a usual catalytic hydrogenation condition can be applied. As to the catalyst to be used in the reaction, metal catalysts such as palladium, palladium-carbon, platinum, Raney-nickel and the like can be exemplified, and such a catalyst is used in usual catalytic quantity. Further, as to the solvent to be used in the reaction, alcohols such as methanol, ethanol, isopropanol and the like; ethers such as dioxane, tetrahydrofuran and the like; aliphatic hydrocarbons such as hexane, cyclohexane and the like; esters such as ethyl acetate; fatty acids such as acetic acid can be exemplified. Said reducing reaction can be carried out either under normal pressure or under high pressure condition, and generally about under normal pressure to 20 kg/cm², preferably under normal pressure to 10 kg/cm². The reaction may be carried out generally at about 0 to 150° C., preferably at about room temperature to 100° C.

The above-mentioned dehydrogenation reaction is carried out in a suitable solvent, by using an oxidizing agent. As to the oxidizing agent, for example benzoquinones such as 2,3-dichloro-5,6-dicyanobenzoquinone, chloranil(2,3,5,6-tetrachlorobenzoquinone) and the like; N-bromosuccinimide, N-chlorosuccinimide, halogenating agents such as bromine and the like; dehydrogenation catalysts such as selenium dioxide, palladium-carbon, palladium-black, palladium oxide, Raney-nickel and the like can be exemplified. The amount of the halogenating agent is not specifically restricted, and can be suitably selected from a wide range, generally about 1 to 5 times, prefereably 1 to 2 times the molar quantities may be used to the starting compound. The dehydrogenation catalyst may be used in a usual catalytic amount. As to the solvent, ethers such as dioxane, tetrahydrofuran, methoxyethanol, dimethoxyethanol and the like; aromatic hydrocarbons such as benzene, toluene, xylene, cumene and the like; halogenated hydrocarbons such as dichloromethan, dichloroethan, chloroform, carbon tetrachloride and the like; alcohols such as butanol, amylalcohol, hexanol and the like; protic polar solvents such as acetic acid; aprotic polar solvents such as dimethylformamide, dimethyl sulfoxide, hexamethylphosphoric trimamide and the like can be exemplified. Said reaction is carried out generally at about room temperature to 300° C., preferably at about room temperature to 200° C., and is completed generally for about 1 to 40 hours.

Among compounds represented by the general formula (1), a compound having acidic group can form a salt with pharmaceutically acceptable basic compound. As to such basic compound for example, metal hydroxides such as sodium hydroxide, potassium hydroxide, lithium hydroxide, calcium hydroxide and the like; carbonates or bicarbonates of alkali metals such as sodium carbonate, sodium hydrogencarbonate and the like; alkali metal alcoholates such as sodium methylate, potassium ethylate and the like can be exemplified. Furthermore, among compounds represented by the general formula (1), a compound having basic group can form a salt with common pharmaceutically acceptable acid. As to such acid for example, inorganic acids such as sulfuric acid, nitric acid, hydrochloric acid, hydrobromic acid and the like; organic acids such as acetic acid, p-toluenesulfonic acid, ethanesulfonic acid, oxalic acid, maleic acid, fumaric acid, citric acid, succinic acid, benzoic acid and the like can be mentioned. These salts can also be used, similar to compounds represented by the general formula (1) in free form, as compounds of effective ingredient in the present invention. Moreover, compounds represented by the general formula (1) involve inevitably their sterioisomers and optical isomers, and these isomers can also be used as compounds of effective ingredients.

The objective compounds prepared by each of these Reaction formulas-1 to -4 can be isolated from the reaction system by common separating methods, and can be further purified. As to methods for separation and purification, for example, distillation, recrystallization, column chromatography, ion-exchange chromatography, gel chromatography, affinity chromatography, preparative thin layer chromatography, solvent extraction and others can be applied.

POSSIBILITY OF INDUSTRIAL UTILIZATION

Benzimidazole derivatives represented by the general formula (1) are used for pharmaceuticals as in the forms of usual general pharmaceutical preparations. Said pharmaceutical preparations are formulated by using usually used diluents such as fillers, bulking fillers, binders, wetting agents, disintegrants, surface active agents, lubricants; or excipients. The pharmaceutical preparations can be selected from various administration forms in accordance with the therapeutic purposes. As to typical administration forms, there can be exemplified tablets, pills, powders, liquids, suspensions, emulsions, granules, capsules, suppositories, injection preparations (liquids, suspensions, etc.) and the like. For the purpose of shaping the administration unit form into the tablets, various carriers which are well-known in this field can be widely used. As to the examples of carriers, excipients such as lactose, white sugar, sodium chloride, glucose, urea, starch, calcium carbonate, kaolin, crystal-line cellulose, silicic acid and the like; binders such as water, ethanol, propanol, simple syrup, glucose solution, starch solution, gelatin solution, carboxymethyl cellulose, shellac, methyl cellulose, potassium phosphate, polyvinylpyrrolidone and the like; disintegrants such as dry starch, sodium alginate, agar-agar powder, laminaran powder, sodium hydrogencarbonate, calcium carbonate, polyoxyethylene sorbitan fatty acid esters, sodium laurylsulfate, monoglyceride of stearic acid, starch, lactose and the like; disintegration inhibitors such as white sugar, stearin, cacao butter, hydrogenated oils and the like; absorption accelerators such as quaternary ammonium salts, sodium laurylsulfate and the like; wetting agents such as glycerin, starch and the like; adsorbents such as starch, lactose, kaolin, bentonite, colloidal silicic acid and the like; lubricants such as refined talc, stearates, boric acid powder, polyethylene glycols and the like can be mentioned. The tablets preparations can be further shaped into tablets coated with usual tablet coating, for example sugar coated tablets, gelatin film coated tablets, tablets coated with enteric coating, tablets coated with film coating, or double layer tablets and multiple layer tablets. For the purpose of shaping the administration unit into pills, various carriers which are well-known in this field can be widely used. As to the examples of carriers, excipients such as glucose, lactose, starch, cacao butter, hydrogenated vegetable oils, kaolin, talc and the like; binders such as powdered acacia, powdered tragacanth, gelatin, ethanol and the like; disintegrants such as laminaran, agar-agar and the like can be exemplified. For the purpose of shaping the administration unit into suppositories, various carriers which are well-known in this field can be widely used. As to the examples of carriers, polyethylene glycols, cacao butter, higher alcohols, esters of higher alcohols, gelatin, semi-synthesized glycerides and the like can be mentioned. For the purpose of shaping the administration unit form into capsules, the benzimidazole derivative as the effective ingredient is mixed with the above-mentioned various carriers and the mixture thus obtained is placed into rigid gelatin capsules or soft capsules. For the purpose of shaping the administration unit into injection preparations, liquid preparations, emulsion preparations and suspension preparations are sterilized, further these preparations are preferably isotonic to the blood, and the all diluents which are conventionally used in this field can also be used for example, water, ethyl alcohol, macrogols, propylene glycol, ethoxylated isostearyl alcohol, polyoxylated isostearyl alcohol, polyoxyethylenesorbitan fatty acid esters can be used. Additionally, for the purpose to prepare isotonic injection solutions, an adequate amount of sodium chloride, glucose or glycerin may be added to the injection preparations, further, usual dissolving additives, buffering agents, local anesthetics and the like may be added. Moreover, if necessary, coloring agents, preservatives, spices, flavors, sweetening agents and others may be added to the pharmaceutical preparations.

The amount of the benzimidazol derivative as effective ingredient to be contained in the pharmaceutical preparation of the present invention is not specifically restricted and can be suitably selected from a wide range, and generally about 1 to 70% by weight, preferably 5 to 50% by weight of the active ingredient may be contained in the pharmaceutical preparations.

Methods for administering the pharmaceutical preparation of the present invention are not restricted, they can be administered in accordance with various forms of preparations, age of the patient, distinguish of sex and other conditions, the degree of the symptom and the like. For example, tablets, pills, liquids, suspensions, emulsions, granules and capsuled are administered orally. While, injection preparations are intravascularly administered, singly or by mixing with common transfusions such as glucose or amino acid solutions, and if necessary, they are singly administered intramuscularly, intracutaneously, subcutaneously or intraperitonealy. Suppositories are administered to the rectum.

Dose of pharmaceutical preparation of the present invention is suitably selected depend on the usage, age of the patient, distinguish of sex and other conditions, and degree of the symptom, and generally the amount of effective compound may be about 0.6 to 50 mg/kg of the body weight per day. The effective compound to be contained in the administration unit form may preferably be in the range of about 10 to 1000 mg.

The amount of compound of the effective ingredient to be formulated in the pharmaceutical preparation for external use of the present invention is not specifically restricted and can be suitably selected from a wide range, generally, 0.01 to 20% by weight, preferably 0.1 to 5% by weight thereof may be formulated.

As to the basic excipients used for external pharmaceutical preparations of the present invention, oily bases and water-soluble bases which are well known in this field can be selected from a wide range, provided that they show not any phamacological activities by themselved. As to the oily bases, specifically oils and fats such as peanut oil, rubber oil, soybean oil, corn oil, rapeseed oil, cottonseed oil, castor oil, camellia oil, coconut oil, olive oil, cacao butter, lanolin, beef tallow, squalane and wool fat and the like; chemically changed such as hydrogenated reformed products of these fats and oils; mineral oils such as vaseline, paraffin, silicone oil; higher fatty acid esters, such as isopropyl myristate, n-butyl myristate, isopropyl linolate, cetyl licinolate, stearyl licinolate, diethyl sebacate, disopropyl adipate; higher aliphatic alcohol such as cetyl alcohol, stearyl alcohol; waxes such as bleched beeswax, spermaceti, Japan wax and the like; higher aliphatic acid such as stearic acid, oleic acid, palmitic acid and the like; mixtures of mono-, di- and tri-glycerides of natural saturated fatty acid having 12 to 18 carbon atoms and the like can be exemplified. Among these fats and oils, the various vegetable oils and the mixtures of mono-, di- and tri-glycerides are especially preferable. Furthermore, as to the water-soluble basic excipients, specifically polyethylene glycol, propylene glycol, glycerin, glycerogelatin, methyl cellulose, hydroxymethyl cellulose, hydroxyethyl cellulose, hydroxypropyl cellulose, hydroxypropylmethyl cellulose, hydroxyvinyl polymer, polyvinyl alcohol and the like can be exemplified. In the present invention, these basic excipients may be used singly or may be used by mixing with 2 or more of them.

In using the pharmaceutical preparations for external use of the present invention, commonly used additives such as water, surface active agents, gelling agents, preservatives, antioxidant, buffering agents, pH controlling agents, wetting agents, antiseptics, coloring agents, fragrant agents and the like can be suitably added thereto in accordance with the necessity.

The form of pharmaceutical preparations for external use of the present invention is not specifically restricted, and in the forms of an ointment, cream, lotions, emulsion and gel are preferably used, such forms of them can be prepared in accordance with usual methods.

EXAMPLES

In order to explain more clearly, the present invention will be illustrated by referring to Examples of pharmaceutical preparations, Reference examples, Examples and Pharmacological tests as follow.

Example of Pharmaceutical Preparation-1

| | |
|---|---|
| 1-Benzyl-6-chloro-2-{1-[3-(1-pyrazolyl)propyl]indol-5-ylaminocarbonyl}benzimidazole | 150 g |

-continued

| | |
|---|---|
| Avicel | 40 g |
| (Trademark for microcrystalline cellulose, manufactured by Asahi Chemical Industry Co. , Ltd.) | |
| Corn starch | 30 g |
| Magnesium stearate | 2 g |
| Hydroxypropylmethylcellulose | 10 g |
| Polyethylene glycol 6000 | 3 g |
| Castor oil | 40 g |
| Ethanol | 40 g |

1-Benzyl-6-chloro-2-{1-[3-(1-pyrazolyl)-propyl]indol-5-ylaminocarbonyl}benzimidazole of the present invention, Avicel, corn starch and magnesium stearate were mixed together and ground, the thus obtained mixture was shaped into the form of tablets by using a conventional pounder (R 10 mm) for sugar coating. The thus obtained tablets were coated with a film coating agent consisting of hydroxypropylmethyl cellulose, poloxyethylene glycol 6000, castor oil and ethanol to prepare film coated tablets.

Example of Pharmaceutical Preparation-2

| | |
|---|---|
| 1-Benzyl-6-chloro-2-[1-isopropyl-tetrazol-5-yl)methyl-3,4-dihydro-2(1H)-quinolinon-6-yl-aminocarbonyl]benzimidazole | 150.0 g |
| Citric acid | 1.0 g |
| Lactose | 33.5 g |
| Dicalcium phosphate | 70.0 g |
| Pluronic F-68 | 30.0 g |
| Sodium laurylsulfate | 15.0 g |
| Polyvinylpyrrolidone | 15.0 g |
| Polyethylene glycol (Carbowax 1500) | 4.5 g |
| Polyehtylene glycol (Carbowax 6000) | 45.0 g |
| Corn starch | 30.0 g |
| Dried sodium stearate | 3.0 g |
| Dried magnesium stearate | 3.0 g |
| Ethanol | q.s. |

1-Benzyl-6-chloro-2-[1-isopropyltetrazol-5-yl)methyl-3, 4-dihydro-2(1H)-quinolinon-6-ylaminocarbonyl] benzimidazole, citric acid, lactose, dicalcium phosphate, Pluronic F-68 and sodium laurylsulfate were mixed together.

The thus obtained mixture was sieved through a sieve of No. 60, the obtained sieved mixture was granulated under wet condition with an alcohol solution containing polyvinylpyrrolidone, Carbowax 1500 and 6000. The granulated product was formed to paste like lump by adding ethanol, as occasion arises. Next, corn starch was added thereto and mixing operation of said mixture was continued until uniform granules were formed. The granules were sieved through a sieve of No. 10, then the sieved granules were placed in a tray and dried at 100° C. in an oven for 12 to 14 hours. The dried granules were sieved through a sieve of No. 16, then dried sodium laurylsulfate and dried magnesium stearysulfate were added to the dried granules. The whole mixture of dried granules were mixed well and were compressed, by using a tablet machine, into the desired shape of tablets to be used for the core portions of coated tablets.

The above-mentioned core portions of the tablets were treated with a varnish, and the surface thereof were coated with talc powder for preventing from the absorption of moisture. The surface of the treated core portions were further coated with a primary coating layer, and were further coated with a varnish to make them having a sufficient number of layers on the surface for preparing coated tablets for oral administration. In order to make the coated core portions of tablets into complete spherical form and to make the treated surface smoothly, the coated tablets were further coated with primary coating layers and smoothing coating layers. The coated tablets were color coated until the desired color of the surface were obtained. After the coated tablets were dried, the surface thereof were polished to make them uniform gloss.

Example of Pharmaceutical Preparation-3

| 1-Benzyl-6-chloro-2-{1-[3-(imidazol-1-yl)propyl]indol-5-ylaminocarbonyl}-benzimidazole | 5.0 g |
|---|---|
| Polyethylene glycol (M.W. 4000) | 0.3 g |
| Sodium chloride | 0.9 g |
| Polyoxyethylene sorbitan monooleate | 0.4 g |
| Sodium metabisulfite | 0.1 g |
| Methylparaben | 0.18 g |
| Propylparaben | 0.02 g |
| Distilled water for injection | 10.0 ml |

The above-mentioned Methylparaben, Propylparaben, sodium metabisulfite and sodium chloride were dissolved in a half volume of the above-mentioned distilled water at 80° C., under stirring. The solution thus obtained was cooled to 40° C., then 1-benzyl-6-chloro-2-{1-[3-(imidazole-1-yl)propyl]indol-5-ylaminocarbonyl}benzimidazole of the effective ingredient of the present invention, next polyethylene glycol and polyoxyethylene sorbitan monooleate were dissolved in this order in the above-mentioned solution. Then to the thus obtained solution was added the remaining volume of distilled water for injection to adjust the final volume of the injection composition into the predetermined volume, then was sterilized by sterilizing filtration by using a suitable filter paper to prepare injection preparation.

Reference Example 1

To 100 ml of acetic acid solution containing 20 g of 2-benzylamino-4-chloroaniline was added 15 ml of O-methyl-trichloroacetoimidate at 0 to 25° C., and stirred the mixture at room temperature for 3 hours. Then water was added to the reaction mixture, the separated crystals were collected by filtration to obtain 29.6 g of 1-benzyl-6-chloro-2-trichloromethylbenzimidazole in the form of pale brown powder.

$^1$H-NMR (250 MHz, DMSO-$d_6$) δ ppm:
5.94 (2H, s), 7.04 (2H, d, J=6.5 Hz), 7.25–7.5 (5H, m), 7.88 (1H, d, J=9.0 Hz).

Reference Example 2

Fifty (50) ml of methanol suspension containing 5 g of 1-benzyl-6-chloro-2-trichloromethylbenzimidazole and 7.7 g of potassium carbonate was heated and refluxed for 24 hours. After the reaction mixture was filtrated, the solvent was removed by distillation under reduced pressure, the residue thus obtained was dissolved in chloroform, then after removal of the insoluble matters by filtration, the solvent was removed by distillation to obtain 4.7 g of 1-benzyl-6-chloro-2-trimethoxymethylbenzimidazole in the form of brown oily substance. Said oily substance was dissolved in 50 ml of acetone, and 1 g of p-toluenesulfonic acid was added, the mixture was refluxed for 2 hours, the solvent was removed under reduced pressure. The residue thus obtained was dissolved in chloroform, and the solution was washed with water, an aqueous solution saturated with sodium hydrogencarbonate, then was dried with anhydrous magnesium sulfate, and the solvent was removed by distillation. The residue was crystallized by using diisopropyl ether-ethyl acetate to obtain 2.84 g of methyl 1-benzyl-6-chlorobenzimidazole-2-carboxylate in the form of light brown powdery product.

Melting point: 184–186° C.

Reference Example 3

To 4.4 g of 5-nitro-1-(3-phthalimidopropyl)-indole was added 200 ml of dimethylformamide, further was added 0.15 g of 10% palladium-carbon and hydrogenized at 65° C., under the pressure of 4 kg/cm$^2$, for 7 hours. After the reaction was finished, the reaction mixture was filtrated, and the solvent was removed by distillation under reduced pressure. The thus obtained residue was treated to a silica column chromatography (eluent: 3% methanol/dichloromethane) to obtain 3.4 g of 5-amino-1-(3-phthalimidopropyl)indole in the form of brown needle crystals.

$^1$H-NMR (250 MHz, CDCl$_3$) δ ppm:
2.16–2.28 (2H, m), 3.73 (2H, t, J=7 Hz), 4.12 (2H, t, J=7 Hz), 6.28 (1H, d, J=3 Hz), 6.64–6.69 (1H, m), 6.9 (1H, d, J=2 Hz), 7.11–7.14 (2H, m), 7.7–7.73 (2H, m), 7.82–7.86 (2H, m).

By using suitable starting materials, and by method similar to that employed in Reference example 3, there were obtained compounds of Reference examples 15–22, 26–33, 47 and 49.

Reference Example 4

To 2.3 g of lithium aluminum hydride was added 100 ml of tetrahydrofuran, under stirring condition, and 6 g of 5-cyano-1-[3-(2-isopropyl-imidazol-1-yl)propyl]indole was gradually added thereto. The mixture was refluxed for 4 hours, then after confirmation of that the reaction was finished, under cooling at 0° C., 2.3 ml of water, 2.3 ml of 10% aqueous solution of potassium hydroxide and 7 ml of water were gradually added thereto. The reaction mixture was diluted with ethyl acetate, then filtrated with Celite, and the solvent was removed by distillation, 5.3 g of 5-aminomethyl-1-[3-(2-isopropylimidazol-1-yl)propyl]indole was obtained in the form of yellow oily product.

$^1$H-NMR (250 MHz, CDCl$_3$) δ ppm:
1.22 (6H, d, J=7 Hz), 2.3–2.4 (2H, m), 2.7–2.8 (2H, m), 3.81 (2H, t, J=7.5 Hz), 3.95 (2H, s), 4.16 (2H, t, J=7 Hz), 6.51 (1H, d, J=3 Hz), 6.77 (1H, d, J=1.5 Hz), 6.98–7.04 (2H, m), 7.19 (2H, s), 7.57 (1H, s).

By using a suitable starting material and by a method similar to that employed in Reference example 4, there was obtained a compound of Reference example 5 shown in Table 1 as follows.

TABLE 1

$$R^3-(A)n-R^{20}$$

| Reference example No. | $R^{20}$ | —(A)n— | $R^3$ | Crystal form |
|---|---|---|---|---|
| 5 | NH$_2$ | —CH$_2$— | 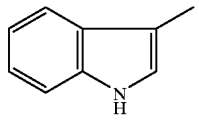 | Brown solid |

Reference Example 6

1.5 Grams of 5-nitroindole was dissolved in 70 ml of dimethylformamide, then 370 mg of sodium hydride (in oil)

was added thereto, the mixture was stirred under nitrogen gas stream at 60° C. for 1 hour. Under cooling at 0° C., 1.63 g of 5-chloromethyl-1-isopropyl-1,2,3,4-tetrazole was added, the reaction mixture was stirred at room temperature for 4.5 hours. After the reaction was finished, water was added to the reaction mixture, then the separated crystals were collected by filtration and washed with water. The crystals were dissolved in dichloromethane, the solution was dried with anhydrous magnesium sulfate, and the solvent was removed by distillation under reduced pressure. The residue obtained was subjected to a silica gel column chromatography (eluent: dichloromethane→3% methanol/ dichloromethane), there was obtained 2.3 g of 1-(1-isopropyl-1,2,3,4-tetrazol-5-ylmethyl)-5-nitroindole as in the form of yellow powder.

$^1$H-NMR (250 MHz, CDCl$_3$) δ ppm:
1.35 (6H, d, J=6.5 Hz), 4.37–4.47 (1H, m), 5.70 (2H, s), 6.79–6.81 (1H, m), 7.27–7.30 (1H, m), 7.48 (1H, d, J=9 Hz), 8.12–8.17 (1H, m), 8.59 (1H, d, J=2 Hz).

By using suitable starting materials and by method similar to that employed in Reference example 6, there were obtained compounds of Reference examples 7 to 49 as shown in Tables 2 to 8 as follows.

TABLE 2

$R^3$—(A)n—$R^{20}$

| Reference example No. | $R^{20}$ | —(A)n— | $R^3$ | Crystal form |
|---|---|---|---|---|
| 7 | NO$_2$ | — | (5-methylindol-1-yl)(CH$_2$)$_3$–(indol-1-yl) | Yellow powdery product |
| 8 | NO$_2$ | — | (5-methylindol-1-yl)(CH$_2$)$_3$–(5-methoxyindol-1-yl) | Yellow powdery product |
| 9 | NO$_2$ | — | (5-methylindol-1-yl)(CH$_2$)$_3$O–(3-cyanophenyl) | Yellow powdery product |
| 10 | NO$_2$ | — | (5-methylindol-1-yl)(CH$_2$)$_3$O–(2-cyanophenyl) | Yellow powdery product |
| 11 | NO$_2$ | — | (5-methylindolin-1-yl)(CH$_2$)$_3$–(1-isopropyl-1,2,3,4-tetrazol-5-yl) | Brown oily product |

TABLE 2-continued
$R^3$—(A)n—$R^{20}$
| Reference example No. | $R^{20}$ | —(A)n— | $R^3$ | Crystal form |
|---|---|---|---|---|
| 12 | NO$_2$ | — | 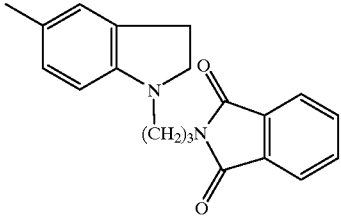 | Brown powdery product |
TABLE 3
$R^3$—(A)n—$R^{20}$
| Reference example No. | $R^{20}$ | —(A)n— | $R^3$ | Crystal form |
|---|---|---|---|---|
| 13 | NO$_2$ | — | 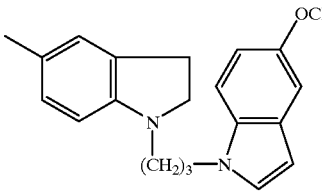 | Dark yellow powdery product |
| 14 | NO$_2$ | — | 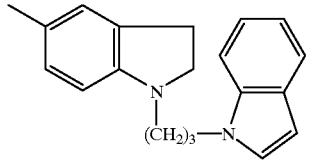 | Dark yellow powdery product |
| 15 | NH$_2$ | — | 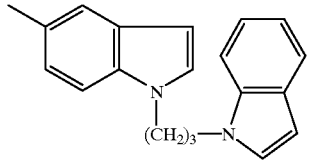 | |
| 16 | NH$_2$ | — | 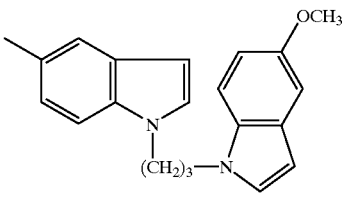 | Brown oily product |
| 17 | NH$_2$ | — | 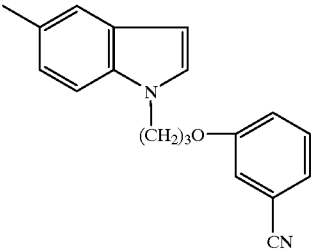 | Pale brown oily product |

TABLE 3-continued
R³—(A)n—R²⁰
| Reference example No. | R²⁰ | —(A)n— | R³ | Crystal form |
|---|---|---|---|---|
| 18 | NH₂ | — | 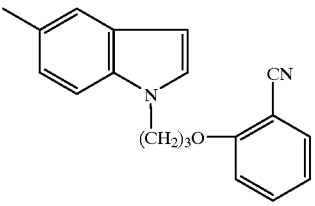 | Pale brown oily product |
TABLE 4
R³—(A)n—R²⁰
| Reference example No. | R²⁰ | —(A)n— | R³ | Crystal form |
|---|---|---|---|---|
| 19 | NH₂ | — | 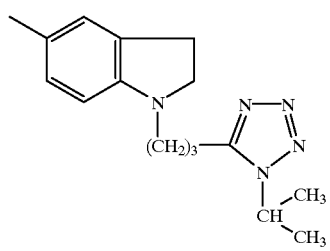 | Black oily product |
| 20 | NH₂ | — | 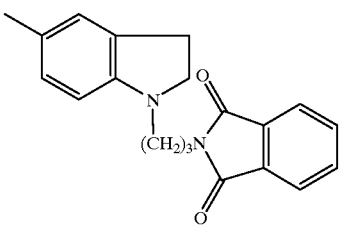 | Brown powdery product |
| 21 | NH₂ | — | 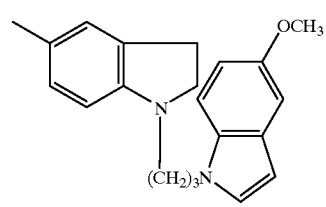 | Dark violet oily product |
| 22 | NH₂ | — | 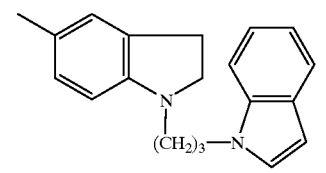 | Dark violet oily product |

TABLE 4-continued
R³—(A)n—R²⁰
| Reference example No. | R²⁰ | —(A)n— | R³ | Crystal form |
|---|---|---|---|---|
| 23 | NH₂ | —CH₂— | 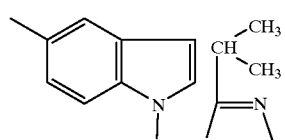 | Yellow oily product |
| 24 | CN | — | | Pale yellow oily product |
TABLE 5
R³—(A)n—R²⁰
| Reference example No. | R²⁰ | —(A)n— | R³ | Crystal form |
|---|---|---|---|---|
| 25 | NH₂ | — | 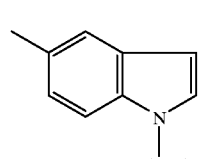 | |
| 26 | NH₂ | — | | Brown oily product |
| 27 | NH₂ | — | | Oily product |
| 28 | NH₂ | — | | Brown oily product |

TABLE 5-continued

R³—(A)n—R²⁰

| Reference example No. | R²⁰ | —(A)n— | R³ | Crystal form |
|---|---|---|---|---|
| 29 | NH₂ | — | 5-methylindoline-N-(CH₂)₃-piperidine-4-ol-4-phenyl | Black oily product |
| 30 | NH₂ | — | 5-methylindole-N-(CH₂)₃-tetrazole-N-CH(CH₃)₂ | Brown oily product |
| 31 | NH₂ | — | 5-methylindole-N-CH₂-tetrazole-N-CH(CH₃)₂ | Brown oily product |

TABLE 6

R³—(A)n—R²⁰

| Reference example No. | R²⁰ | —(A)n— | R³ | Crystal form |
|---|---|---|---|---|
| 32 | NH₂ | — | 5-methylindole-N-(CH₂)₃-phthalimide | Brown needle crystals |
| 33 | NH₂ | — | 5-methylindole-N-(CH₂)₃-5,6-dimethylbenzimidazole | Brown oily product |

TABLE 6-continued
R³—(A)n—R²⁰
| Reference example No. | R²⁰ | —(A)n— | R³ | Crystal form |
|---|---|---|---|---|
| 34 | NO₂ | — | 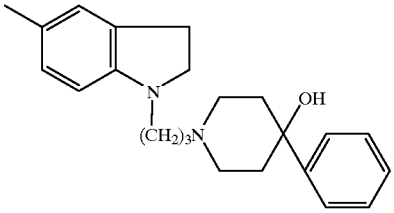 | Yellow powdery product |
| 35 | NO₂ | — | 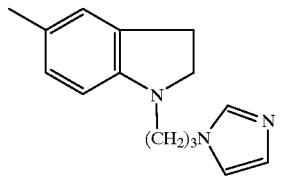 | Yellow powdery product |
| 36 | NO₂ | — | 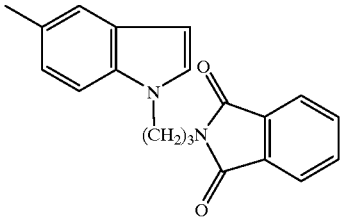 | Yellow powdery product |
| 37 | NO₂ | — | 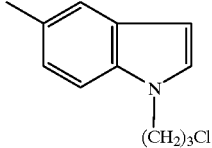 | Yellow powdery product |
| 38 | NO₂ | — | 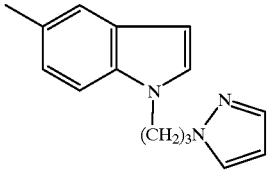 | Yellow powdery product |
TABLE 7
R³—(A)n—R²⁰
| Reference example No. | R²⁰ | —(A)n— | R³ | Crystal form |
|---|---|---|---|---|
| 39 | NO₂ | — | 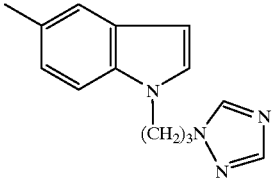 | Yellow powdery product |

TABLE 7-continued
R³—(A)n—R²⁰
| Reference example No. | R²⁰ | —(A)n— | R³ | Crystal form |
|---|---|---|---|---|
| 40 | NO₂ | — | 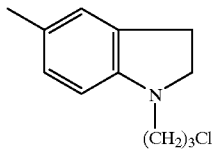 | Yellow oily product |
| 41 | NO₂ | — | 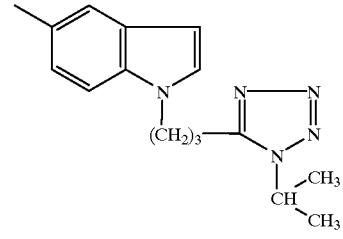 | Yellow oily product |
| 42 | NO₂ | — | 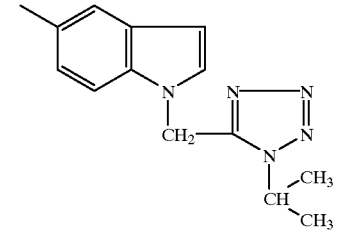 | Yellow powdery product |
| 43 | NO₂ | — | 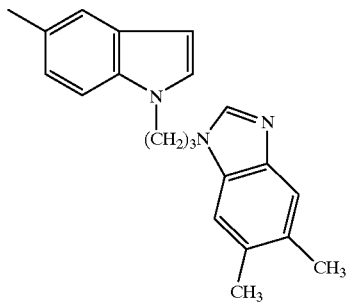 | Yellow powdery product |
| 44 | CN | — | 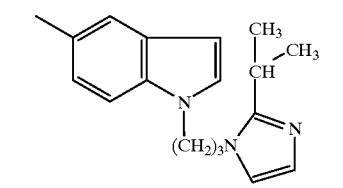 | Pale yellow oily product |
| 45 | NO₂ | — | 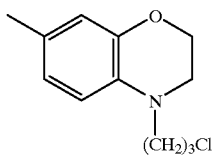 | Brown powdery product |

TABLE 8

R³—(A)n—R²⁰

| Reference example No. | R²⁰ | —(A)n— | R³ | Crystal form |
|---|---|---|---|---|
| 46 | NO₂ | — | 7-methyl-4-(3-imidazol-1-yl-propyl)-2,3-dihydro-1,4-benzoxazine | Yellow solid product |
| 47 | NH₂ | — | 7-methyl-4-(3-imidazol-1-yl-propyl)-2,3-dihydro-1,4-benzoxazine | Black oily product |
| 48 | NO₂ | — | 7-methyl-4-(3-phthalimidopropyl)-2,3-dihydro-1,4-benzoxazine | Yellow powdery product |
| 49 | NH₂ | — | 7-methyl-4-(3-phthalimidopropyl)-2,3-dihydro-1,4-benzoxazine | Dark brown oily product |

The NMR spectrum data of compounds obtained in the above-mentioned Reference examples are shown as follows.

Compound of Reference Example 5
¹H-NMR (250 MHz, CDCl₃) δ ppm:
1.60 (2H, brs), 4.07 (2H, d, J=1 Hz), 7.10–7.26 (3H, m), 7.36–7.39 (1H, m), 7.65–7.68 (1H, m) 8.12 (1H, brs).

Compound of Reference Example 7
¹H-NMR (250 MHz, DMSO-d₆) δ ppm:
2.2–2.4 (2H, m), 4.20 (2H, t, J=7.5 Hz), 4.29 (2H, t, J=7.5 Hz), 6.44 (1H, d, J=3 Hz), 6.77 (1H, d, J=3 Hz), 7.0–7.2 (2H, m), 7.35–7.45 (2H, m), 7.5–7.75 (3H, m), 7.97–8.02 (1H, m), 8.58 (1H, d, J=2 Hz).

Compound of Reference Example 8
¹H-NMR (250 MHz, CDCl₃) δ ppm:
2.4–2.5 (2H, m), 3.86 (3H, s), 4.07–4.13 (4H, m), 6.47 (1H, t, J=2.5 Hz), 6.69 (1H, d, J=3.5 Hz), 6.83–6.88 (1H, m), 7.01 (1H, d, J=3 Hz), 7.07–7.18 (4H, m), 8.06 (1H, dd, J=2.5 Hz, 9 Hz), 8.59 (1H, d, J=2.5 Hz).

Compound of Reference Example 9
¹H-NMR (250 MHz, DMSO-d₆) δ ppm:
2.2–2.3 (2H, m), 3.97 (2H, t, J=6 Hz), 4.46 (2H, t, J=7 Hz), 6.77 (1H, d, J=3 Hz), 7.23–7.27 (1H, m), 7.37–7.51 (3H, m), 7.67–7.72 (2H, m), 7.98 (1H, dd, J=2 Hz, 9 Hz), 8.57 (1H, d, J=2 Hz).

Compound of Reference Example 10
¹H-NMR (250 MHz, DMSO-d₆) δ ppm:
2.25–2.35 (2H, m), 4.07 (2H, t, J=6 Hz), 4.48 (2H, t, J=7 Hz), 6.78 (1H, d, J=3 Hz), 7.07–7.19 (2H, m), 7.61–7.78 (4H, m), 8.0 (1H, dd, J=2 Hz, 9 Hz), 8.58 (1H, d, J=2 Hz).

Compound of Reference Example 11
¹H-NMR (250 MHz, CDCl₃) δ ppm:
1.57 (6H, d, J=6.5 Hz), 2.2–2.3 (2H, m), 2.89 (2H, t, J=7 Hz), 3.08 (2H, t, J=9 Hz), 3.44 (2H, t, J=7 Hz), 3.67 (2H, t, J=9 Hz), 4.4–4.6 (1H, m), 6.24 (1H, d, J=9 Hz), 7.85–7.9 (1H, m), 7.99–8.03 (1H, m).

Compound of Reference Example 12
¹H-NMR (250 MHz, DMSO-d₆) δ ppm:
1.9–2.0 (2H, m), 3.01 (2H, t, J=8.5 Hz), 3.37 (2H, t, J=9 Hz), 3.66 (4H, m), 6.51 (1H, d, J=9 Hz), 7.78–7.96 (6H, m).

Compound of Reference Example 13
¹H-NMR (250 MHz, DMSO-d₆) δ ppm:
2.0–2.1 (2H, m), 3.02 (2H, t, J=8.5 Hz), 3.25 (2H, t, J=7.5 Hz), 3.62 (2H, t, J=8.5 Hz), 3.74 (3H, s), 4.21 (2H, t, J=7

Hz), 6.30–6.35 (2H, m), 6.73–6.78 (1H, m), 7.05 (1H, d, J=2.5 Hz), 7.32 (1H, d, J=3 Hz), 7.38 (1H, d, J=9 Hz), 7.80 (1H, s), 7.90–7.95 (1H, m).

Compound of Reference Example 14
$^1$H-NMR (250 MHz, DMSO-$d_6$) δ ppm:
2.0–2.1 (2H, m), 3.02 (2H, t, J=8.5 Hz), 3.27 (2H, t, J=7.5 Hz), 3.62 (2H, t, J=9 Hz), 4.26 (2H, t, J=7 Hz), 6.34 (1H, d, J=9 Hz), 6.44–6.45 (1H, m), 6.98–7.15 (2H, m), 7.38 (1H, d, J=3 Hz), 7.48–7.56 (2H, m), 7.80 (1H, d, J=2.5 Hz), 7.93 (1H, dd, J=2.5 Hz, 9 Hz).

Compound of Reference Example 15
$^1$H-NMR (250 MHz, CDCl$_3$) δ ppm:
2.35–2.45 (2H, m), 4.00–4.11 (4H, m), 6.33–6.34 (1H, m), 6.52 (1H, d, J=3 Hz), 6.64–6.68 (1H, m), 6.94–7.22 (7H, m), 7.64 (1H, d, J=7.5 Hz).

Compound of Reference Example 16
$^1$H-NMR (250 MHz, CDCl$_3$) δ ppm:
2.35–2.45 (2H, m), 3.85 (3H, s), 3.99–4.07 (4H, m), 6.33 (1H, d, J=3 Hz), 6.43 (1H, d, J=3 Hz), 6.64–6.68 (1H, m), 6.83–6.88 (1H, m), 6.94–6.97 (2H, m), 7.01–7.04 (2H, m), 7.10–7.13 (2H, m).

Compound of Reference Example 17
$^1$H-NMR (250 MHz, CDCl$_3$) δ ppm:
2.25–2.35 (2H, m), 3.4–3.6 (2H, br), 3.85 (2H, t, J=6 Hz), 4.30 (2H, t, J=6.5 Hz), 6.28–6.30 (1H, m), 6.62–6.66 (1H, m), 6.92–6.97 (2H, m), 7.0–7.15 (3H, m), 7.23–7.26 (1H, m), 7.33–7.39 (1H, m)

Compound of Reference Example 18
$^1$H-NMR (250 MHz, CDCl$_3$) δ ppm:
2.3–2.4 (2H, m), 3.3–3.7 (2H, br), 3.89 (2H, t, J=8 Hz), 4.38 (2H, t, J=8 Hz), 6.26 (1H, d, J=3 Hz), 6.6–6.7 (1H, m), 6.75–6.81 (1H, m), 6.91 (1H, s), 7.0–7.1 (2H, m), 7.17–7.20 (1H, m), 7.4–7.5 (1H, m), 7.58 (1H, d, J=8 Hz).

Compound of Reference Example 19
$^1$H-NMR (250 MHz, CDCl$_3$) δ ppm:
1.55 (6H, d, J=6.5 Hz), 2.1–2.25 (2H, m), 2.8–3.4 (8H, m), 4.51–4.62 (1H, m), 6.2–6.6 (3H, m)

Compound of Reference Example 20
$^1$H-NMR (250 MHz, CDCl$_3$) δ ppm:
1.92–2.04 (2H, m), 2.6–3.5 (8H, brm), 3.83 (2H, t, J=7 Hz), 6.3–6.6 (3H, m), 7.67–7.86 (4H, m).

Compound of Reference Example 21
$^1$H-NMR (250 MHz, CDCl$_3$) δ ppm:
2.0–2.2 (2H, m), 2.8–3.0 (4H, m), 3.19 (2H, t, J=8 Hz), 3.86 (3H, s), 4.25 (2H, t, J=6.5 Hz), 6.2–6.3 (1H, m), 6.4–6.5 (2H, m), 6.57 (1H, s), 6.84–6.88 (1H, m), 7.08–7.11 (2H, m), 7.26 (1H, t, J=5 Hz).

Compound of Reference Example 22
$^1$H-NMR (250 MHz, CDCl$_3$) δ ppm:
2.1–2.2 (2H, m), 2.8–3.0 (4H, m), 3.20 (2H, t, J=8 Hz), 4.29 (2H, t, J=7 Hz), 6.2–6.3 (1H, m), 6.4–6.6 (3H, m), 7.1–7.3 (3H, m), 7.38 (1H, d, J=8 Hz), 7.64 (1H, d, J=7.5 Hz).

Compound of Reference Example 23
$^1$H-NMR (250 MHz, CDCl$_3$) δ ppm:
1.22 (6H, d, J=7 Hz), 2.3–2.4 (2H, m), 2.7–2.8 (2H, m), 3.81 (2H, t, J=7.5 Hz), 3.95 (2H, s), 4.16 (2H, t, J=7 Hz), 6.51 (1H, d, J=3 Hz), 6.77 (1H, d, J=1.5 Hz), 6.98–7.04 (2H, m), 7.19 (2H, s), 7.57 (1H, s).

Compound of Reference Example 24
$^1$H-NMR (250 MHz, CDCl$_3$) δ ppm:
2.23–2.33 (2H, m), 3.45 (2H, t, J=6 Hz), 4.38 (2H, t, J=6.5 Hz), 6.60 (1H, d, J=3.5 Hz), 7.2 (1H, s), 7.44 (2H, d, J=1 Hz), 7.98 (1H, t, J=1 Hz).

Compound of Reference Example 25
$^1$H-NMR (250 MHz, CDCl$_3$) δ ppm:
2.6–2.7 (2H, m), 2.8–2.9 (2H, m), 3.55 (2H, brs), 4.4–4.6 (2H, m), 5.1–5.3 (2H, m), 5.8–6.0 (1H, m), 6.5–6.6 (2H, m), 6.8–6.9 (1H, m).

Compound of Reference Example 26
$^1$H-NMR (250 MHz, CDCl$_3$) δ ppm:
2.36–2.46 (2H, m), 3.3–3.7 (2H, br), 4.0–4.1 (4H, m), 6.2–6.4 (2H, m), 6.6–6.7 (1H, m), 6.93 (1H, d, J=2 Hz), 7.0–7.1 (2H, m), 7.30 (1H, d, J=2 Hz), 7.56 (1H, d, J=1.5 Hz).

Compound of Reference Example 27
$^1$H-NMR (250 MHz, CDCl$_3$) δ ppm:
2.4–2.6 (2H, m), 3.1–3.8 (2H, br), 4.1–4.3 (4H, m), 6.33 (1H, d, J=3 Hz), 6.68 (1H, dd, J=8.5 Hz, 2 Hz), 6.9–7.1 (3H, m), 7.97 (2H, d, J=12 Hz).

Compound of Reference Example 28
$^1$H-NMR (250 MHz, CDCl$_3$) δ ppm:
2.0–2.1 (2H, m), 2.85–2.9 (4H, m), 3.19 (2H, t, J=9 Hz), 4.11 (2H, t, J=7 Hz), 6.25 (1H, d, J=8 Hz), 6.45–6.5 (1H, m), 6.5–6.6 (1H, m), 6.93 (1H, s), 7.08 (1H, s), 7.49 (1H, s).

Compound of Reference Example 29
$^1$H-NMR (250 MHz, CDCl$_3$) δ ppm:
1.7–2.0 (4H, m), 2.2–2.4 (2H, m), 2.5–2.7 (4H, m), 2.9–3.0 (4H, m), 3.01 (2H, t, J=7 Hz), 3.24 (2H, t, J=8 Hz), 6.37 (1H, d, J=8 Hz), 6.4–6.5 (1H, m), 6.56 (1H, s), 7.3–7.4 (3H, m), 7.52 (2H, d, J=7 Hz).

Compound of Reference Example 30
$^1$H-NMR (250 MHz, CDCl$_3$) δ ppm:
1.43 (6H, d, J=6.5 Hz), 2.4–2.5 (2H, m), 2.59 (2H, t, J=8 Hz), 4.1–4.2 (1H, m), 4.29 (2H, t, J=6.5), 6.3 (1H, d, J=2.5 Hz), 6.62–6.66 (1H, m), 6.92–7.03 (3H, m).

Compound of Reference Example 31
$^1$H-NMR (250 MHz, CDCl$_3$) δ ppm:
1.25 (6H, d, J=6.5 Hz), 4.2–4.3 (1H, m), 5.57 (2H, s), 6.4 (1H, d, J=3 Hz), 6.64–6.69 (1H, m), 6.9 (1H, d, J=2 Hz), 6.99 (1H, d, J=3 Hz), 7.1 (1H, d, J=8.5 Hz).

Compound of Reference Example 32
$^1$H-NMR (250 MHz, CDCl$_3$) δ ppm:
2.16–2.28 (2H, m), 3.73 (2H, t, J=7 Hz), 4.12 (2H, t, J=7 Hz), 6.28 (1H, d, J=3 Hz), 6.64–6.69 (1H, m), 6.9 (1H, d, J=2 Hz), 7.11–7.14 (2H, m), 7.7–7.73 (2H, m), 7.82–7.86 (2H, m).

Compound of Reference Example 33
$^1$H-NMR (250 MHz, CDCl$_3$) δ ppm:
2.35–2.5 (8H, m), 4.0–4.1 (4H, m), 6.35 (1H, d, J=2.5 Hz), 6.67–6.70 (1H, m), 6.96–7.06 (4H, m), 7.57 (1H, s), 7.70 (1H, s).

Compound of Reference Example 34
$^1$H-NMR (250 MHz, CDCl$_3$) δ ppm:
1.5–1.7 (1H, br), 1.76–1.87 (4H, m), 2.1–2.2 (2H, m), 2.43–2.5 (4H, m), 2.7–2.8 (2H, m), 3.08 (2H, t, J=8.5 Hz), 3.33 (2H, t, J=7 Hz), 3.68 (2H, t, J=8.5 Hz), 6.32 (1H, d, J=9

Hz), 7.2–7.4 (3H, m), 7.52 (2H, d, J=7HZ), 7.88 (1H, s), 8.02–8.06 (1H, m).

Compound of Reference Example 35
¹H-NMR (250 MHz, CDCl₃) δ ppm:
2.1–2.18 (2H, m), 3.09 (2H, t, J=8.5 Hz), 3.20 (2H, t, J=7 Hz), 3.59 (2H, t, J=8.5 Hz), 4.07 (2H, t, J=7 Hz), 6.17 (1H, d, J=9 Hz), 6.92 (1H, t, J=1.5 Hz), 7.12 (1H, s), 7.48 (1H, s), 7.91 (1H, s), 8.02–8.06 (1H, m).

Compound of Reference Example 36
¹H-NMR (250 MHz, DMSO-d₆) δ ppm:
2.1–2.2 (2H, m), 3.61 (2H, t, J=7 Hz), 4.36 (2H, t, J=7 Hz), 6.75 (1H, d, J=2.5 Hz), 7.71–7.76 (2H, m), 7.8–7.9 (4H, m), 7.99–8.04 (1H, m), 8.55 (1H, d, J=2 Hz).

Compound of Reference Example 37
¹H-NMR (250 MHz, DMSO-d₆) δ ppm:
2.18–2.29 (2H, m), 3.57 (2H, t, J=6.5 Hz), 4.40 (2H, t, J=7 Hz), 6.78 (1H, d, J=3 Hz), 7.62–7.73 (2H, m), 8.02–8.06 (1H, m), 8.57 (1H, d, J=2 Hz).

Compound of Reference Example 38
¹H-NMR (250 MHz, CDCl₃) δ ppm:
2.40–2.51 (2H, m), 4.11 (2H, t, J=6.5 Hz), 4.19 (2H, t, J=7 Hz), 6.31 (1H, t, J=2 Hz), 6.69–6.71 (1H, m), 7.24–7.34 (3H, m), 7.59 (1H, d, J=1.5 Hz), 8.08–8.13 (1H, m), 8.59 (1H, d, J=2 Hz).

Compound of Reference Example 39
¹H-NMR (250 MHz, DMSO-d₆) δ ppm:
2.2–2.4 (2H, m), 4.19 (2H, t, J=7 Hz), 4.32 (2H, t, J=7 Hz), 6.77 (1H, d, J=3 Hz), 7.65–7.68 (2H, m), 7.99–8.06 (2H, m), 8.50 (1H, s), 8.58 (1H, d, J=2 Hz).

Compound of Reference Example 40
¹H-NMR (250 MHz, CDCl₃) δ ppm:
2.0–2.1 (2H, m), 3.09 (2H, t, J=8 Hz), 3.4–3.5 (2H, m), 3.6–3.7 (4H, m), 6.33–6.38 (1H, m), 7.89 (1H, s), 8.03–8.08 (1H, m).

Compound of Reference Example 41
¹H-NMR (250 MHz, CDCl₃) δ ppm:
1.5 (6H, d, J=6.5 Hz), 2.4–2.6 (2H, m), 2.68 (2H, t, J=6.5 Hz), 4.3–4.4 (1H, m), 4.47 (2H, t, J=6.5 Hz), 6.71 (1H, d, J=3 Hz), 7.2–7.3 (2H, m), 8.0–8.1 (1H, m), 8.59 (1H, d, J=2 Hz).

Compound of Reference Example 42
¹H-NMR (250 MHz, CDCl₃) δ ppm:
1.35 (6H, d, J=6.5 Hz), 4.37–4.47 (1H, m), 5.70 (2H, s), 6.79–6.81 (1H, m), 7.27–7.30 (1H, m), 7.48 (1H, d, J=9 Hz), 8.12–8.17 (1H, m), 8.59 (1H, d, J=2 Hz).

Compound of Reference Example 43
¹H-NMR (250 MHz, CDCl₃) δ ppm:
2.33 (3H, s), 2.37 (3H, s), 2.45–2.56 (2H, m), 4.09–4.20 (4H, m), 6.74 (1H, d, J=3 Hz), 6.94 (1H, s), 7.15–7.21 (2H, m), 7.58 (1H, s), 7.72 (1H, s), 8.05–8.09 (1H, m), 8.60 (1H, d, J=2 Hz).

Compound of Reference Example 44
¹H-NMR (250 MHz, CDCl₃) δ ppm:
1.22 (6H, d, J=7 Hz), 2.3–2.4 (2H, m), 2.6–2.8 (1H, m), 3.84 (2H, t, J=7 Hz), 4.19 (2H, t, J=7 Hz), 6.63 (1H, d, J=3 Hz), 6.78 (1H, d, J=1.5 Hz), 7.01 (1H, d, J=1.5 Hz), 7.16 (1H, d, J=3.5 Hz), 7.2–7.3 (1H, m), 7.4–7.5 (1H, m), 8.0 (1H, s).

Compound of Reference Example 45
¹H-NMR (250 MHz, CDCl₃) δ ppm:
2.1–2.2 (2H, m), 3.5–3.7 (6H, m), 4.2–4.3 (2H, m), 6.63 (1H, d, J=9 Hz), 7.67 (1H, d, J=2.5 Hz), 7.78–7.87 (1H, m).

Compound of Reference Example 46
¹H-NMR (250 MHz, CDCl₃) δ ppm:
2.1–2.2 (2H, m), 3.3–3.4 (4H, m), 4.06 (2H, t, J=6.5 Hz), 4.23 (2H, t, J=4.5 Hz), 6.42 (1H, d, J=9 Hz), 6.95 (1H, s), 7.13 (1H, s), 7.50 (1H, s), 7.67 (1H, d, J=2.5 Hz), 7.78 (1H, d, J=2.5 Hz, 9 Hz).

Compound of Reference Example 47
¹H-NMR (250 MHz, CDCl₃) δ ppm:
2.0–2.1 (2H, m), 3.1–3.2 (4H, m), 4.04 (2H, t, J=7 Hz), 4.22 (2H, t, J=4.5 Hz), 6.2–6.3 (2H, m), 6.35–6.45 (1H, m), 6.93 (1H, s), 7.09 (1H, s), 7.49 (1H, s).

Compound of Reference Example 48
¹H-NMR (250 MHz, CDCl₃) δ ppm:
2.0–2.1 (2H, m), 3.4–3.5 (4H, m), 3.78 (2H, t, J=7 Hz), 4.25 (2H, t, J=4.5 Hz), 6.56 (1H, d, J=9 Hz), 7.64 (1H d, J=2.5 Hz), 7.73–7.88 (5H, m).

Compound of Reference Example 49
¹H-NMR (250 MHz, CDCl₃) δ ppm:
1.95–2.04 (2H, m), 3.17–3.23 (4H, m), 3.77 (2H, t, J=7 Hz), 4.22 (2H, t, J=4.5 Hz), 6.2–6.24 (2H, m), 6.5–6.55 (1H, m), 7.7–7.74 (2H, m), 7.83–8.02 (2H, m).

Reference Example 50

To 926 mg of 5-methoxyindole was added 30 ml of dimethylformamide and 230 mg of sodium hydride (in oil), this mixture was stirred under nitrogen gas stream at 60° C. for 1 hour. Then 1.5 g of 1-(3-chloropropyl)-5-nitroindole was added to the reaction mixture and stirred at room temperature overnight. The reaction mixture was further stirred at 60° C. for 5.5 hours, then water was added thereto, and the crystals being separated were collected by filtration, and washed with water. The washed crystals were subjected to a silica gel column chromatography (eluent: dichloromethane), there was obtained 1.8 g of 1-[3-(5-methoxyindol-1-yl)propyl]-5-nitroindole as in the form of yellow powdery product.
¹H-NMR (250 MHz, CDCl₃) δ ppm:
2.4–2.5 (2H, m), 3.86 (3H, s), 4.07–4.13 (4H, m), 6.47 (1H, t, J=2.5 Hz), 6.69 (1H, d, J=3.5 Hz), 6.83–6.88 (1H, m), 7.01 (1H, d, J=3 Hz), 7.07–7.18 (4H, m), 8.06 (1H, dd, J=2.5 Hz, J=9 Hz), 8.59 (1H, d, J=2.5 Hz).

By using suitable starting materials, and by a method similar to that employed in Reference example 50, there were obtained compounds of the above-mentioned Reference examples 7, 9, 10, 12–18, 20–23, 26–29, 32–36, 38, 39, 43, 44 and 46–49.

Reference Example 51

To 500 ml of ethanol solution containing 26 g of 2-benzylamino-4-chloroaniline was added 45.7 g of polymer form (45–50% toluene solution) of ethyl glyoxylate, further 28.4 g of iodine was added and the reaction mixture was stirred at room temperature for 20 minutes. Then 27.8 g of sodium thiosulfate aqueous solution was added thereto, the crystals being separated were collected by filtration, and washed with water and ethanol, then dried. There was obtained 26.1 g of ethyl 1-benzyl-6-chlorobenzimidazol-2-carboxylate as in the form of pale brown powdery product.
¹H-NMR (250 MHz, CDCl₃) δ ppm:

1.45 (3H, t, J=7 Hz), 4.49 (2H, q, J=7 Hz), 5.85 (2H, s), 7.1–7.5 (7H, m), 7.85 (1H, d, J=8.5 Hz).

By using a suitable starting material, and by a method similar to that employed in Reference example 51, compound of the above-mentioned Reference example 2 was obtained.

Example 1A

A mixture of 2.2 g of methyl 1-benzyl-6-chlorobenzimidazol-2-carboxylate and 5.3 g of 1-[3-(2-isopropylimidazol-1-yl)propyl]-5-aminomethylindole was stirred at 80° C. for 1.5 hours, after confirmed that the starting materials were disappeared, the reaction mixture was dissolved in chloroform, then washed with water and an aqueous solution saturated with sodium chloride, and dried with anhydrous magnesium sulfate, then the solvent was removed by distillation under reduced pressure. The resulting residue was subjected a silica gel column chromatography (eluent: 3% methanol/dichloromethane), then fumaric acid was added and recrystallized from diisopropyl ether-ethanol, there was obtained 4 g of 1-benzyl-6-chloro-2-{1-[3-(2-isopropylimidazol-1-yl)propyl indol-5-ylmethylaminocarbonyl}benzimidazole·fumarate as in the form of pale yellow powdary product.

$^1$H-NMR (250 MHz, DMSO-$d_6$) δ ppm:
1.10 (6H, d, J=7 Hz), 2.1–2.3 (2H, m), 2.8–2.95 (1H, m), 3.88 (2H, t, J=7.5 Hz), 4.20 (2H, t, J=7 Hz), 4.55 (2H, d, J=6.5 Hz), 5.98 (2H, s), 6.43 (1H, d, J=3 Hz), 6.62 (2H, s), 6.66 (1H, d, J=1.5 Hz), 7.10 (1H, d, J=1.5 Hz), 7.15–7.38 (10H, m), 7.53 (1H, s), 7.77 (1H, d, J=8.5 Hz), 7.84 (1H, d, J=1.5 Hz), 9.57 (1H, t, J=4 Hz)

Example 1B

130 Milligrams of lithium aluminum hydride was suspended in 70 ml of tetrahydrofuran, then 2.2 g of 6-amino-3,4-dihydro-2(1H)-quinolinone was added gradually thereto, and the mixture was stirred at room temperature overnight. The reaction mixture was further stirred for 2 hours under refluxing condition, then 1 g of methyl 1-benzyl-6-chlorobenzimidazol-2-carboxylate was added, the reaction was continued by refluxing for 3 hours. After the reaction was finished, then water and 10% aqueous solution of potassium hydroxide were added, the reaction mixture was diluted with ethyl acetate and filtered with Celite, and the filtrate was washed with chloroform, the solvent was removed by distillation under reduced pressure. To the residue thus obtained was added ethanol and heated, the insoluble matters were collected by filtration and recrystallized from dimethylformamide, there was obtained 0.11 g of 1-benzyl-6-chloro-2-(3,4-dihydro-2(1H)-quinolinon-6-ylaminocarbonyl)benzimidazole as in the form of yellow powdery product.

Melting point: Higher than 290° C. $^1$H-NMR (250 MHz, DMSO-$d_6$) δ ppm:
2.44 (2H, t, J=7 Hz), 2.87 (1H, t, J=7 Hz), 5.99 (2H, s), 6.83 (1H, d, J=9 Hz), 7.21–7.40 (6H, m), 7.57–7.6 (1H, m), 7.72 (1H, s), 7.86–7.88 (2H, m), 10.08 (1H, s).

Example 1C

To 2.2 g of 5-amino-1-[3-(1-isopropyl-5-tetrazolyl) propyl]indole was added 40 ml of toluene, then this mixture was stirred under nitrogen gas atmosphere by cooling in a methanol-ice bath. To this reaction mixture was added 4 ml of n-hexane solution of 2M trimethylaluminum dropwise from syringe, then reaction mixture was stirred for 20 minutes, and further stirred at room temperature for 1 hour.

2.18 Grams of methyl 1-benzyl-6-chlorobenzimidazol-2-carboxylate was added to the reaction mixture and was stirred for 5 to 6 hours under refluxing condition. Next, 10% hydrochloric acid was added, and the crystals being separated were collected by filtration. Water-chloroform was added to the crystals, this solution was made alkaline with 10% aqueous solution of potassium hydroxide, then was filtered with Celite, the chloroform layer was washed with water, an aqueous solution saturated with sodium chloride. The chloroform layer was dried with anhydrous magnesium sulfate and the solvent was removed under reduced pressure. The residue thus obtained was subjected to a silica gel column chromatography (eluent: 3% methanol/dichloromethane), and recrystallized from ethyl acetate-n-hexane, there was obtained 2.27 g of 1-benzyl-6-chloro-2-{1-[3-(1-isopropyltetrazol-5-yl)propyl]indol-5-ylaminocarbonyl}benzimidazole as in the form of yellow needle crystals.

Melting point: 190–191° C.

By using suitable starting materials, and by methods similar to those employed in Examples 1A to 1C, there were obtained compounds of Examples 2 to 50 as shown in Tables 9 to 33 as follows.

TABLE 9

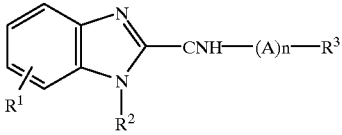

Example 2

| Structure | $R^3$: | 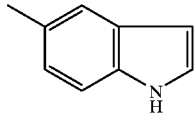 |
| --- | --- | --- |
| | $R^1$: | 6-Cl |
| | $R^2$: | —CH$_2$— 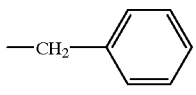 |
| | —(A)n—: | — |
| Crystal form: | | Brown granules |
| Recrystallization solvent: | | Ethyl acetate |
| Melting point: | | 205–207° C. |
| Form of compound: | | Free form |

Example 3

| Structure | $R^3$: | 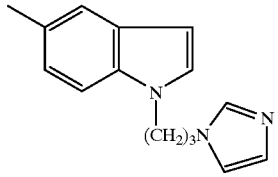 |
| --- | --- | --- |
| | $R^1$: | 6-Cl |

TABLE 9-continued

Structure: benzimidazole with R¹, R²(N-substituent), -C(=N)NH-(A)n-R³

R²: -CH₂-C₆H₅ (benzyl)

—(A)n—: —
Crystal form: Pale yellow needles
Recrystallization solvent: Methanol
Melting point: 187–188° C.
Form of compound: Free form

TABLE 10

Example 4

Structure R³: 5-methylindole with N-(CH₂)₃N(CH₃)(cyclohexyl)

R¹: 6-Cl

R²: -CH₂-C₆H₅

—(A)n—: —
Crystal form: Pale yellow needles
Recrystallization solvent: Ethanol
Melting point: 129–130° C.
Form of compound: Free form

Example 5

Structure R³: 5-methylindole with N-CH₂CH=CH₂

R¹: 6-Cl

R²: -CH₂-C₆H₅

—(A)n—: —
Crystal form: Colorless needles
Recrystallization solvent: Ethyl acetate-ethanol

TABLE 10-continued

Melting point: 154–155° C.
Form of compound: Free form

TABLE 11

Example 6

Structure R³: 5-methylindole with N-(CH₂)₃-pyrazole

R¹: 6-Cl

R²: -CH₂-C₆H₅

—(A)n—: —
Crystal form: Pale yellow needles
Recrystallization solvent: Chloroform-ethyl acetate
Melting point: 165–166° C.
Form of compound: Free form

Example 7

Structure R³: 5-methylindole with N-(CH₂)₃-1,2,4-triazole

R¹: 6-Cl

R²: -CH₂-C₆H₅

—(A)n—: —
Crystal form: Yellow needles
Recrystallization solvent: Methanol-ethyl acetate
Melting point: 196–197° C.
Form of compound: Free form

TABLE 12

Example 8

Structure R³: 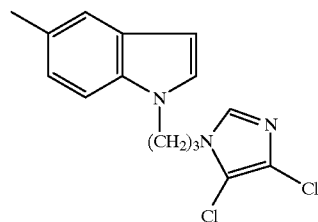

R¹: 6-Cl

R²: 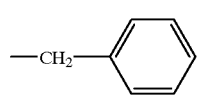

—(A)n—: —
Crystal form: Brown granules
Recrystallization solvent: Ethyl acetate-n-hexane
Melting point: 191–192° C.
Form of compound: Free form

Example 9

Structure R³: 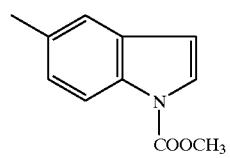

R¹: 6-Cl

R²: 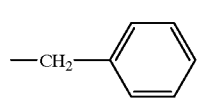

—(A)n—: —
Crystal form: Pale brown powdery
Recrystallization solvent: Ethyl acetate-diisopropyl ether
Melting point: 194–195° C.
Form of compound: Free form

TABLE 13

Example 10

Structure R³: 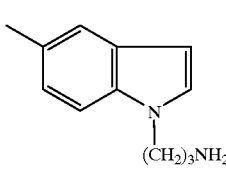

R¹: 6-Cl

TABLE 13-continued

R²: 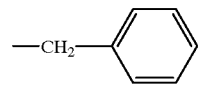

—(A)n—: —
Crystal form: Yellow granules
Recrystallization solvent: Ethyl acetate-n-hexane
Melting point: 106–108° C.
Form of compound: Free form

Example 11

Structure R³: 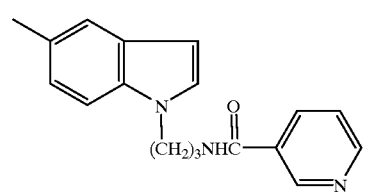

R¹: 6-Cl

R²: 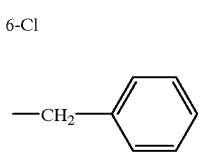

—(A)n—: —
Crystal form: Yellow needles
Recrystallization solvent: Cloroform
Melting point: 206–207° C.
Form of compound: Free form

TABLE 14

Example 12

Structure R³: 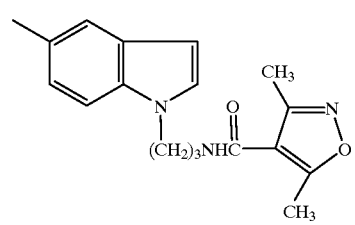

R¹: 6-Cl

R²: 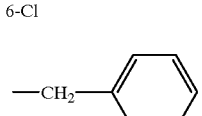

—(A)n—: —
Crystal form: Yellow needles
Recrystallization solvent: Dimethylformamide-water
Melting point: 217–218° C.
Form of compound: Free form TABLE 14-continued Example 13

Structure  R³:

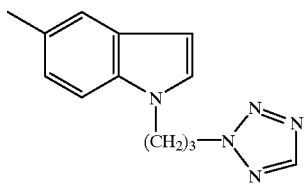

R¹:  6-Cl

R²:

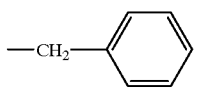

—(A)n—: —
Crystal form: Pale yellow needles
Recrystallization solvent: Dichloromethane-n-hexane
Melting point: 146–147° C.
Form of compound: Free form

TABLE 15

Example 14

Structure  R³:

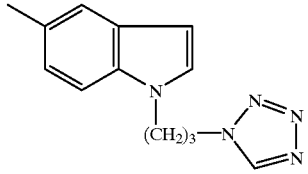

R¹:  6-Cl

R²:

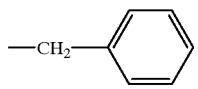

—(A)n—: —
Crystal form: Colorless needles
Recrystallization solvent: Ethyl acetate-n-hexane
Melting point: 178–179° C.
Form of compound: Free form Example 15

Structure  R³:

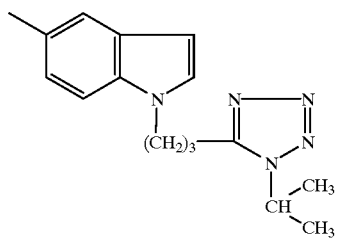

R¹:  6-Cl

R²:

—CH₂—⌬

—(A)n—: —
Crystal form: Yellow needles
Recrystallization solvent: Ethyl acetate-n-hexane
Melting point: 190–191° C.
Form of compound: Free form

TABLE 16

Example 16

Structure  R³:

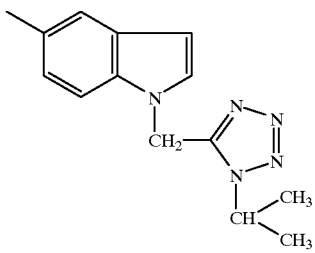

R¹:  6-Cl

R²:

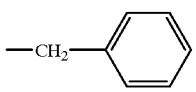

TABLE 16-continued

—(A)n—: —
Crystal form: Pale yellow needles
Recrystallization solvent: Ethyl acetate
Melting point: 229–231° C. (decomposed)
Form of compound: Free form

Example 17

Structure  R³:

[Structure: 5-methylindole connected via N–(CH₂)₃– to N of 5,6-dimethylbenzimidazole]

R¹: 6-Cl

R²: —CH₂—C₆H₅

—(A)n—: —
Crystal form: Pale yellow powdery
Recrystallization solvent: Ethyl acetate
Melting point: 197–198° C.
Form of compound: Free form

TABLE 17

Example 18

Structure  R³:

[Structure: 5-methylindole connected via N–(CH₂)₃– to N of 2-isopropylimidazole]

R¹: 6-Cl

R²: —CH₂—C₆H₅

—(A)n—: —
Crystal form: Pale yellow powdery
Recrystallization solvent: Ethanol-diisopropyl ether Form of compound: [cyclobutane-1,3-dicarboxylic acid structure with two CO₂H groups]

TABLE 17-continued

Example 19

Structure  R³:

[Structure: 5-methylindoline connected via N–(CH₂)₃– to N of imidazole]

R¹: 6-Cl

R²: —CH₂—C₆H₅

—(A)n—: —
Crystal form: Yellow powdery
Recrystallization solvent: Methanol-diisopropyl ether
Melting point: 189–190° C.

TABLE 17-continued

Form of compound: 1½

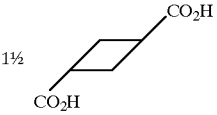

TABLE 18

Example 20

Structure R³:

R¹: 6-Cl

R²:

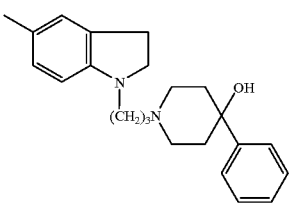

—(A)n—: —
Crystal form: Yellow needles
Recrystallization solvent: Chloroform
Melting point: 186–187° C.
Form of compound: Free form Example 21

Structure R³:

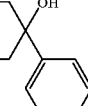

R¹: 6-Cl

R²:

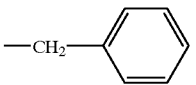

—(A)n—: —
Crystal form: Pale brown powdery
Recrystallization solvent: Ethanol-ethyl acetate
Melting point: 277° C.
Form of compound: Free form

TABLE 19

Example 22

Structure R³:

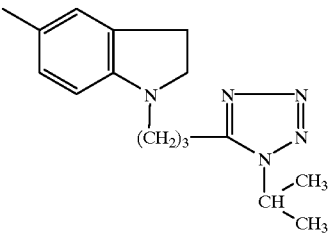

R¹: 6-Cl

R²:

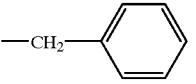

—(A)n—: —
Crystal form: Yellow needles
Recrystallization solvent: Ethyl acetate-ethanol
Melting point: 155–156° C.
Form of compound: Free form Example 23

Structure R³:

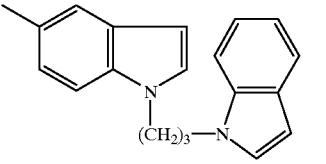

R¹: 6-Cl

R²:

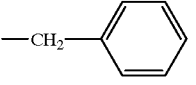

—(A)n—: —
Crystal form: White powdery
Recrystallization solvent: Ethyl acetate
Melting point: 160–161° C.
Form of compound: Free form

TABLE 20

Example 24

Structure R³:

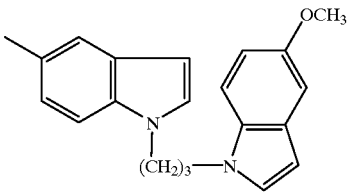

R¹: 6-Cl

TABLE 20-continued

R²: —CH₂—C₆H₅

—(A)n—: —
Crystal form: Yellow powdery
Recrystallization solvent: Ethyl acetate-dichloromethane
Melting point: 169–170° C.
Form of compound: Free form

Example 25

Structure R³: 5-methyl-1-[(CH₂)₃O-(3-cyanophenyl)]-indole

R¹: 6-Cl
R²: —CH₂—C₆H₅

—(A)n—: —
Crystal form: Pale yellow powdery
Recrystallization solvent: Ethyl acetate-n-hexane
Melting point: 166–167° C.
Form of compound: Free form

TABLE 21

Example 26

Structure R³: 5-methyl-1-[(CH₂)₃-O-(2-cyanophenyl)]-indole

R¹: 6-Cl
R²: —CH₂—C₆H₅

—(A)n—: —
Crystal form: Pale brown needles
Recrystallization solvent: Ethyl acetate-n-hexane
Melting point: 156° C.
Form of compound: Free form

TABLE 21-continued

Example 27

Structure R³: 5-methyl-1-[(CH₂)₃N-(5-methoxyindol-1-yl)]-indoline

R¹: 6-Cl
R²: —CH₂—C₆H₅

—(A)n—: —
Crystal form: Bright yellow needles
Recrystallization solvent: Ethyl acetate-n-hexane
Melting point: 157° C.
Form of compound: Free form

TABLE 22

Example 28

Structure R³: 5-methyl-1-[(CH₂)₃NHC(O)-pyrrol-2-yl]-indoline

R¹: 6-Cl
R²: —CH₂—C₆H₅

—(A)n—: —
Crystal form: Yellow granules
Recrystallization solvent: Dimethylformamide-water
Melting point: 213–221° C.
Form of compound: Free form

Example 29

Structure R³: 5-methyl-1-[(CH₂)₃N-(indolin-1-yl)]-indoline

R¹: 6-Cl

TABLE 22-continued

R²: —CH₂—C₆H₅ (benzyl)

—(A)n—: —
Crystal form: Bright yellow needles
Recrystallization solvent: Ethyl acetate-n-hexane
Melting point: 136–137° C.
Form of compound: Free form

TABLE 23

Example 30

Structure  R³: 3-methylindol-1-yl (indole with methyl at 3-position, attached via N-H)

R¹: 6-Cl

R²: —CH₂—C₆H₅

—(A)n—: —
Crystal form: Colorless granules
Recrystallization solvent: Ethyl acetate
Melting point: 187–188° C.
Form of compound: Free form

Example 31

Structure  R³: 3-methylindole with N-(CH₂)₃-imidazol-1-yl substituent

R¹: 6-Cl

R²: —CH₂—C₆H₅

—(A)n—: —
Crystal form: White amorphous
Form of compound: Hydrochloride

TABLE 24

Example 32

Structure  R³: 3-methylindol-1-yl (N-H)

R¹: 6-Cl

R²: —CH₂—C₆H₅

—(A)n—: —
Crystal form: Colorless needles
Recrystallization solvent: Ethyl acetate-n-hexane
Melting point: 173–174° C.
Form of compound: Free form

Example 33

Structure  R³: 5-methylindoline with N-(CH₂)₃NHC(O)-(3,5-dimethylisoxazol-4-yl)

R¹: 6-Cl

R²: —CH₂—C₆H₅

—(A)n—: —
Crystal form: Yellow powdery
Recrystallization solvent: Ethanol-n-hexane
Melting point: 153–155° C.
Form of compound: Free form

TABLE 25

Example 34

Structure  R³: 5-methylindoline with N-(CH₂)₃NHC(O)-(pyridin-2-yl)

R¹: 6-Cl

R²: —CH₂—C₆H₅

TABLE 25-continued

—(A)n—: —
Crystal form: Yellow needles
Recrystallization solvent: Ethyl acetate
Melting point: 139–140° C.
Form of compound: Free form

Example 35

Structure  $R^3$:

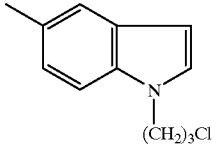

$R^1$: 6-Cl $R^2$:

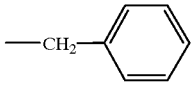

—(A)n—: —
Form of compound: Free form

TABLE 26

Example 36

Structure  $R^3$:

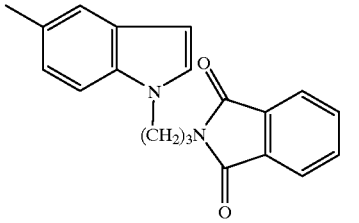

$R^1$: 6-Cl $R^2$:

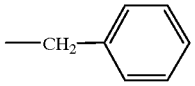

—(A)n—: —
Crystal form: Yellow needles
Form of compound: Free form

Example 37

Structure  $R^3$:

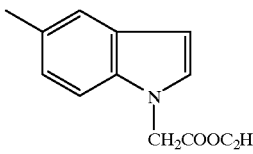

$R^1$: 6-Cl

TABLE 26-continued $R^2$:

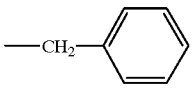

—(A)n—: —
Form of compound: Free form

TABLE 27

Example 38

Structure  $R^3$:

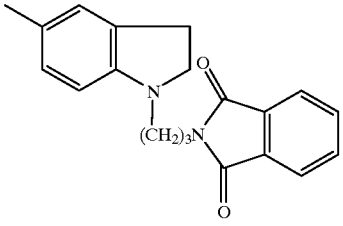

$R^1$: 6-Cl $R^2$:

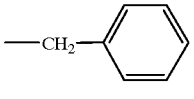

—(A)n—: —
Crystal form: Brown solid
Form of compound: Free form

Example 39

Structure  $R^3$:

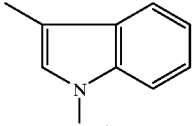

$R^1$: 6-Cl $R^2$:

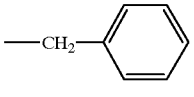

—(A)n—: —
Crystal form: Plae yellow oily
Form of compound: Free form

TABLE 28

Example 40

Structure  $R^3$:

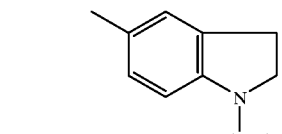

TABLE 28-continued

Example 40 (continued)

R¹: 6-Cl

R²: —CH₂—C₆H₅

—(A)n—: —
Crystal form: Yellow powdery
Form of compound: Free form

Example 41

Structure R³:

6-methyl-3,4-dihydroquinolin-2(1H)-one (N—H)

R¹: 6-Cl

R²: —CH₂—C₆H₅

—(A)n—: —
Crystal form: Yellow powdery
Recrystallization solvent: Dimethylformamide
Melting point: Higher than 290° C.
Form of compound: Free form

TABLE 29

Example 42

Structure R³:

6-methyl-1-(CH₂CH=CH₂)-3,4-dihydroquinolin-2(1H)-one

R¹: 6-Cl

R²: —CH₂—C₆H₅

—(A)n—: —
Crystal form: Yellow powdery
Recrystallization solvent: Ethyl acetate-n-hexane
Melting point: 183–184° C.
Form of compound: Free form

TABLE 29-continued

Example 43

Structure R³:

6-methyl-1-[(CH₂)₃-imidazol-1-yl]-3,4-dihydroquinolin-2(1H)-one

R¹: 6-Cl

R²: —CH₂—C₆H₅

—(A)n—: —
Crystal form: Pale yellow powdery
Recrystallization solvent: Ethyl acetate
Melting point: 195° C.
Form of compound: Free form

TABLE 30

Example 44

Structure R³:

6-methyl-1-[(CH₂)₃N(CH₃)(CH₂)₂N(CH₃)₂]-3,4-dihydroquinolin-2(1H)-one

R¹: 6-Cl

R²: —CH₂—C₆H₅

—(A)n—: —
Crystal form: Yellow powdery
Recrystallization solvent: Ethanol
Melting point: 200–202° C.
Form of compound: 2 · (cyclobutane-1,3-dicarboxylic acid, CO₂H / CO₂H)

TABLE 30-continued

Example 45

Structure R³:

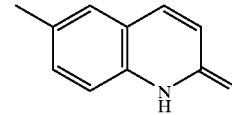

R¹: 6-Cl

R²:

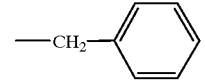

—(A)n—: —
Crystal form: Colorless needles
Recrystallization solvent: Ethyl acetate-ethanol
Melting point: 227–228° C.
Form of compound: Free form

TABLE 31

Example 46

Structure R³:

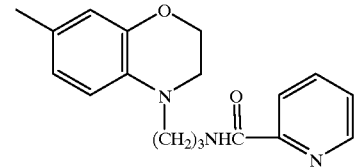

R¹: 6-Cl

R²:

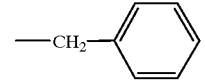

—(A)n—: —
Crystal form: Pale brown powdery
Recrystallization solvent: Chloroform-isopropyl alcohol
Melting point: Higher than 290° C.
Form of compound: Free form

Example 47

Structure R³:

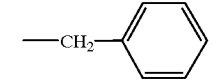

R¹: 6-Cl

TABLE 31-continued

R²:

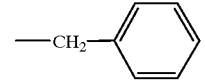

—(A)n—: —
Crystal form: Bright yellow needles
Recrystallization solvent: Ethyl acetate-diisopropyl ether
Melting point: 146–148° C.
Form of compound: Free form

TABLE 32

Example 48

Structure R³:

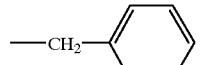

R¹: 6-Cl

R²:

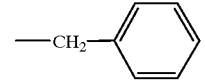

—(A)n—: —
Crystal form: Yellow powdery
Recrystallization solvent: Ethyl acetate-n-hexane
Melting point: 175–176° C.
Form of compound: Free form

Example 49

Structure R³:

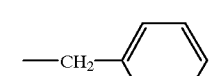

R¹: 6-Cl

R²:

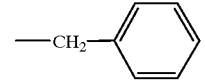

—(A)n—: —
Form of compound: Free form

TABLE 33

Example 50

Structure R³:

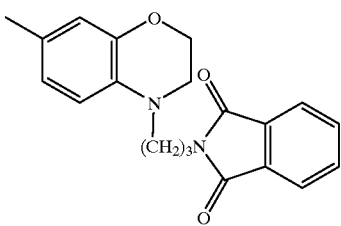

R¹: 6-Cl

R²:
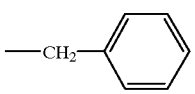

—(A)n—: —
Crystal form: Yellow amorphous
Form of compound: Free form

The NMR spectrum data of compounds obtained in the above-mentioned Examples are shown as follow.

Compound of Example 18
¹H-NMR (250 MHz, DMSO-$d_6$) δ ppm: 1.10 (6H, d, J=7 Hz), 2.1–2.3 (2H, m), 2.8–2.95 (1H, m), 3.88 (2H, t, J=7.5 Hz), 4.20 (2H, t, J=7 Hz), 4.55 (2H, d, J=6.5 Hz), 5.98 (2H, s), 6.43 (1H, d, J=3 Hz), 6.62 (2H, s), 6.66 (1H, d, J=1.5 Hz), 7.10 (1H, d, J=1.5 Hz), 7.15–7.38 (10H, m), 7.53 (1H, s), 7.77 (1H, d, J=8.5 Hz), 7.84 (1H, d, J=1.5 Hz), 9.57 (1H, d, J=4 Hz).

Compound of Example 28
¹H-NMR (250 MHz, DMSO-$d_6$) δ ppm:
1.7–1.9 (2H, m), 2.89 (2H, t, J=8 Hz), 3.07 (2H, t, J=7.5 Hz), 3.2–3.4 (4H, m), 5.99 (2H, s), 6.0–6.1 (1H, m), 6.47 (1H, d, J=8.5 Hz), 6.7–6.8 (1H, m), 6.8–6.9 (1H, m), 7.2–7.5 (7H, m), 7.57 (1H, s), 7.8–7.9 (2H, m), 8.0–8.1 (1H, m)

Compound of Example 31
¹H-NMR (250 MHz, DMSO-$d_6$) δ ppm:
2.25–2.4 (2H, m), 2.9–3.1 (2H, m), 3.5–3.65 (2H, m), 4.1–4.3 (4H, m), 5.97 (2H, s), 7.02 (1H, t, J=7.5 Hz), 7.11–7.43 (9H, m), 7.60–7.64 (2H, m), 7.71–7.75 (2H, m), 7.81 (1H, d, J=1.5 Hz), 9.09 (1H, s), 9.25 (1H, t, J=8 Hz).

Compound of Example 35
¹H-NMR (250 MHz, CDCl₃) δ ppm:
2.2–2.35 (2H, m), 3.4–3.5 (2H, m), 4.3–4.4 (2H, m), 6.05 (2H, s), 6.5–6.6 (1H, m), 7.1–7.2 (1H, m), 7.2–7.5 (9H, m), 7.7–7.8 (1H, m), 8.1–8.2 (1H, m), 9.62 (1H, s).

Compound of Example 36
¹H-NMR (250 MHz, CDCl₃) δ ppm:
2.26 (2H, m), 3.75 (2H, t, J=7 Hz), 4.2 (2H, t, J=7 Hz), 6.06 (2H, s), 6.48 (1H, d, J=3 Hz), 7.24–7.5 (10H, m), 7.7–7.86 (5H, m), 8.07 (1H, s), 9.60 (1H, s).

Compound of Example 37
¹H-NMR (250 MHz, CDCl₃) δ ppm:
1.26 (3H, t, J=7 Hz), 4.15–4.3 (2H, m), 4.84 (2H, s), 6.06 (2H, s), 6.56 (1H, d, J=3 Hz), 7.12 (1H, d, J=3 Hz), 7.23–7.47 (7H, m), 7.75 (1H, d, J=8.5 Hz), 8.12 (1H, s), 9.62 (1H, s).

Compound of Example 38
¹H-NMR (250 MHz, CDCl₃) δ ppm:
1.95–2.1 (2H, m), 2.92 (2H, t, J=8.5 Hz), 3.13 (2H, t, J=7 Hz), 3.36 (2H, t, J=8 Hz), 3.83 (2H, t, J=7.5 Hz), 6.02 (2H, s), 6.44 (1H, d, J=8.5 Hz), 7.25–7.33 (7H, m), 7.39 (1H, d, J=1.5 Hz), 7.52 (1H, s), 7.69–7.73 (3H, m), 7.82–7.85 (2H, m), 9.40 (1H, s).

Compound of Example 39
¹H-NMR (250 MHz, CDCl₃) δ ppm:
2.2–2.3 (2H, m), 3.10 (2H, t, J=7 Hz), 3.44 (2H, t, J=6 Hz), 3.75–3.85 (2H, m), 4.30 (2H, t, J=6 Hz), 5.97 (2H, s), 7.03 (1H, s), 7.12–7.37 (10H, m), 7.61–7.66 (2H, m), 7.8–7.9 (1H, m).

Compound of Example 40
¹H-NMR (250 MHz, CDCl₃) δ ppm:
1.31 (2H, brs), 1.70–1.81 (2H, m), 2.83 (2H, t, J=7 Hz), 2.97 (2H, t, J=8 Hz), 3.12 (2H, t, J=7.5 Hz), 3.36 (2H, t, J=8 Hz), 6.02 (2H, s), 6.45 (1H, d, J=8.5 Hz), 7.23–7.32 (7H, m), 7.38 (1H, d, J=2 Hz), 7.53 (1H, s), 7.71 (1H, d, J=9 Hz), 9.43 (1H, s).

Compound of Example 41
¹H-NMR (250 MHz, DMSO-$d_6$) δ ppm:
2.44 (2H, t, J=7 Hz), 2.87 (2H, t, J=7 Hz), 5.99 (2H, s), 6.83 (1H, d, J=9 Hz), 7.21–7.40 (6H, m), 7.57–7.6 (1H, m), 7.72 (1H, s), 7.86–7.88 (2H, m), 10.08 (1H, s).

Compound of Example 46
¹H-NMR (250 MHz, DMSO-$d_6$) δ ppm
6.01 (2H, s), 6.50 (1H, d, J=9.5 Hz), 7.22–7.41 (7H, m), 7.84–7.93 (4H, m), 8.25 (1H, s).

Compound of Example 49
¹H-NMR (250 MHz, DMSO-$d_6$) δ ppm:
1.9–2.1 (2H, m), 2.5–2.6 (2H, m), 2.8–3.0 (2H, m), 3.6–3.8 (2H, m), 3.9–4.1 (2H, m), 5.99 (2H, s), 7.1–7.5 (7H, m), 7.6–8.0 (4H, m).

Compound of Example 50
¹H-NMR (250 MHz, CDCl₃) δ ppm:
1.9–2.1 (2H, m), 3.28–3.34 (4H, m), 3.77 (2H, t, J=7 Hz), 4.26 (2H, t, J=4 Hz), 6.01 (2H, s), 6.63 (1H, d, J=9 Hz), 7.11–7.40 (9H, m), 7.70–7.74 (3H, m), 7.81–7.87 (2H, m), 9.34 (1H, s).

Example 51

To 0.66 g of 1-benzyl-6-chloro-2-(indol-5-ylaminocarbonyl)benzimidazole was added 50 ml of dimethylformamide, further added 170 mg of oily sodium hydride, said mixture was stirred under nitrogen gas atmosphere at 60° C. for 1 hour. Under cooling at 0° C., 0.14 ml of allyl bromide was added to the reaction mixture, and stirred at room temperature overnight, then water was added thereto and extracted with ethyl acetate, the extract was washed with water and an aqueous solution saturated with sodium chloride. The washed extract was dried with anhydrous magnesium sulfate, and the solvent was removed by distillation under reduced pressure. The residue thus obtained was subjected to a silica gel column chromatography (eluent: 10% n-hexane/dichloromethane), recrystallized from ethyl acetate-ethanol, there was obtained 0.35 g of 1-benzyl-6-chloro-2-(1-allylindol-5-ylaminocarbonyl) benzimidazole as in the form of colorless needle crystals.

Melting point: 154–155° C.

By using suitable starting materials and by a method similar to that of employed in Example 51, there were obtained compounds of the above-mentioned Examples 3, 4, 6–8, 10–20, 22–29, 31, 33–40, 42–45 and 47–50.

Example 52

To 3.8 g of 1-benzyl-6-chloro-2-[1-(3-chloro-propyl) indol-5-ylaminocarbonyl]benzimidazole was added 100 mg of dimethylformamide, further added 1.4 g of 1H-1,2,3,4-tetrazol, 2.2 g of potassium carbonate and 7.2 g of sodium iodide, the mixture was heated and stirred at 100° C. for 2 days. Water was added to the reaction mixture, and extracted with ethyl acetate, the extract was washed with water and an aqueous solution saturated with sodium chloride. The washed extract was dried with anhydrous magnesium sulfate, and the solvent was removed by distillation under reduced pressure. The residue thus obtained was subjected to a silica gel column chromatography (eluent: ethyl acetate/n-hexane=1/1), after separation of isomers, there were obtained 1.1 g of 1-benzyl-6-chloro-2-{1-[3-(1,2,3,4-tetrazol-1-yl)propyl]indol-5-ylaminocarbonyl}benzimidazole (A) as in form of colorless needle crystals by recrystallization from ethyl acetate-n-hexane, and 0.9 g of 1-benzyl-6-chloro-2-{1-[3-(1,2,3,4-tetrazol-2-yl)-propyl]indol-5-ylaminocarbonyl}benzimidazole (B) as in the form of pale yellow needle crystals by recrystallization from dichloromethane-n-hexane.

Melting point of (A): 178–179° C.

Melting point of (B): 146–147° C.

By using suitable starting materials, and by a method similar to that of employed in Example 52, there were obtained compounds of the above-mentioned Examples 3, 4, 6–8, 10–12, 17–20, 23–29, 31, 33, 34, 36, 38, 40, 43, 44, 47, 48 and 50.

Example 53

To 5 g of 1-benzyl-6-chloro-2-[1-(3-phthalimidopropyl) indol-5-ylaminocarbonyl]benzimidazole was added 100 ml of ethanol and stirred, then 0.5 ml of hydrazine hydrate was added thereto, the mixture was refluxed overnight. After cooled the reaction mixture to room temperature, then white crystals were removed by filtration. Water was added to the filtrate, and made alkaline with 10% aqueous solution of potassium hydroxide. This mixture was extracted with dichloromethane, the extract was washed with water, an aqueous solution saturated with sodium chloride then was dried with anhydrous magnesium sulfate. The solvent was removed by distillation under reduced pressure. The residue thus obtained was crystallized from ethyl acetate-n-hexane, there was obtained 3.2 g of 1-benzyl-6-chloro-2-[1-(3-aminopropyl)indol-5-ylaminocarbonyl]-benzimidazole as in the form of yellow granular crystals. Melting point: 106–108° C.

By using a suitable starting material, and a method similar to that of employed in Example 53, there was obtained compound of the above-mentioned Example 40.

Example 54

To 0.29 g of nicotinic acid was added 50 ml of dimethylformamide, further 1.2 g of 1-benzyl-6-chloro-2-[1-(3-aminopropyl)indol-5-ylaminocarbonyl]-benzimidazole and 0.7 ml of triethylamine were added, the mixture was stirred under cooling at 0° C. Next, 0.49 g of diethylcyanophosphonate was dissolved in 20 ml of dimethylformamide and added thereto and the reaction mixture was stirred at room temperature for 1 day. After the reaction was finished, water was added then the whole mixture was extracted with ethyl acetate, the extract thus obtained was washed with water and an aqueous solution saturated with sodium chloride. The washed extract was dried with anhydrous magnesium sulfate, then the solvent was removed by distillation under reduced pressure. The resulting residue was subjected to a silica gel column chromatography (eluent: 2% methanol/dichloromethane), recrystallized from chloroform, there was obtained 1 g of 1-benzyl-6-chloro-2-{1-[3-(pyridin-3-ylcarbonylamino)propyl]indol-5-ylaminocarbonyl}benzimidazole as in the form of yellow needle crystals.

Melting point: 206–207° C.

By using suitable starting materials and a method similar to that of employed in example 54, there were obtained compounds of the above-mentioned Examples 9, 12, 28, 33, 34 and 47.

Example 55

To 0.35 g of 1-benzyl-6-chloro-2-(3,4-dihydro-2(1H)-quinolinon-6-ylaminocarbonyl)-benzimidazole was added 30 ml of dioxane and 280 mg of 2,3-dichloro-5,6-dicyanobenzoquinone, and the reaction mixture was refluxed by heating. Over confirming the proceeding of reaction by means of a thin layer chromatography, 2,3-dichloro-5,6-dicyanobenzoquinone in small quantity was further added and refluxed by heating for 1 day. The crystals being separated were collected by filtration, and recrystallized from chloroform-isopropyl alcohol, there was obtained 1-benzyl-6-chloro-2-[2(1H)-quinolinon-6-ylamino-caronyl]benzimidazole as in the form of pale brown powdery product.

Melting point: higher than 290° C. $^1$H-NMR (250 MHz, DMSO-$d_6$) δ ppm:

6.01 (2H, s), 6.50 (1H, d, J=9.5 Hz), 7.22–7.41 (7H, m), 7.84–7.93 (4H, m), 8.25 (1H, s).

Example 56

A mixture of 27.9 g of ethyl 1-benzyl-6-chlorobenzimidazol-2-carboxylate, 17.8 g of 1-[3-(imidazol-1-yl)propyl]-5-aminoindole, 8 g of sodium methylate and 600 ml of toluene was stirred at 100° C. for 1.5 hours. The reaction mixture was cooled to room temperature, the crystals being separated were collected by filtration and washed with toluene. Thus obtained crystals were dissolved in 500 ml of chloroform, then 100 ml of water was added and the mixture was filtrated with Celite. The chloroform layer was taken by separation, after washed with water, the chloroform portion layer was dried with anhydrous magnesium sulfate, and the solvent was removed by distillation to obtain brown oily product. This oily product was dissolved in methanol, further added n-hexane and the crystals being separated were collected by filtration, recrystallized from methanol and dried. There was obtained 31.8 g of 1-benzyl-6-chloro-2-{1-[3-(imidazol-1-yl)propyl]indol-5-ylamino-carbonyl}benzimidazole.

Pale yellow needle crystals.

Melting point: 187–188° C.

By using suitable starting materials, and by a method similar to that of employed in Example 56, there were obtained compounds of the above-mentioned Examples 2 and 4–50.

Pharmacological Tests (1) Measurement of the Activity for Inhibiting cGMP PDE Separation and partial purification of PDE (phosphodiesterase) from human platelets, and measurement of the activity for inhibiting cGMP PDE were conducted by the method of Hidaka, et al. [Biochimica et Biophysica Acta, Vol. 429, (1976), pp. 485–497]. The platelets obtained from human healthy adult were washed, and suspended in TRIS-buffer solution, then said suspension was treated by centrifugal separation, the supernatant was subjected to a DEAE-cellulose treatment and fractionated into FI to FIII fractions by a method of concentration gradient of sodium acetate. Thus obtained FI fraction was used as the sample of cGMP-PDE. The activity for inhibiting cGMP-PDE was measured by using 0.4 $\mu$M of [$^3$H]-cGMP.

The results are shown in Table 34 as follows.

TABLE 34

| Test compound of: | Activity for inhibiting cGMP-PDE [IC$_{50}$ ($\mu$M)] |
|---|---|
| Example 2 | 0.02 |
| Example 3 | 0.01 |
| Example 4 | 0.06 |
| Example 9 | 0.08 |
| Example 11 | 0.01 |
| Example 20 | 0.01 |
| Example 21 | 0.02 |
| Example 25 | 0.12 |
| Example 28 | <0.01 |
| Example 31 | 0.03 |
| Example 32 | 0.06 |
| Example 33 | <0.01 |
| Example 41 | 0.02 |
| Example 42 | 0.1 |
| Example 44 | 0.014 |
| Example 46 | <0.01 |
| Example 47 | <0.01 |

(2) Measurement of the Activity for Inhibiting Proliferation of Rat A10 Cells

Test was conducted by the modified method of N. Morisaki [Atherosclerosis, Vol. 71, (1988), pp. 165–171]. The rat A10 cells (purchased from Dainippon Pharmaceutical Co., Ltd.) were inoculated on a 24 wells immunoplate at a density of 10,000 cells/well, and were cultured in 10% FBS (fetal bovine serum) for 2 days, and in order to introduce the cells into the resting stage, the cells were further cultured in a serum-free medium for 2 days. After that, 1% FBS was added thereto for stimulating the proliferation, of the cells and at the same time, a test compound and 0.5 $\mu$Ci/well of [$^3$H]-thymidine were added. As to the index of synthesized amount of DNA, the quantity of [$^3$H]-thymidine being uptaken by the cells was measured at the time of 24 hours after the final cultivation was started.

The results are shown in Table 35 as follows.

TABLE 35

| Test compound of: | Activity for inhibiting proliferation of rat A10 cells [IC$_{50}$ ($\mu$M)] |
|---|---|
| Example 2 | 0.4 |
| Example 3 | 0.5 |
| Example 4 | 0.3 |
| Example 6 | 0.66 |
| Example 7 | 0.49 |
| Example 11 | 0.97 |
| Example 12 | 0.69 |
| Example 18 | 0.48 |
| Example 20 | 0.85 |
| Example 32 | 0.24 |
| Example 33 | 1.27 |
| Example 42 | 0.95 |
| Example 47 | 0.67 |

(3) Measurement of the Activity for Inhibiting Proliferation of the Human Fibroblast Similar to the activity for inhibiting proliferation of rat A10 cells as mentioned above, the activity for inhibiting proliferation of the human fibroblast (purchased from Dainippon Pharmaceutical Co., Ltd.) was determined by measuring the uptake amount of [$^3$H]-thymidine. Compounds of Examples 3, 16, 31, 33, 45 and 47 were used for the test, and the measured values of IC$_{50}$ were, 0.04 $\mu$M, 0.049 $\mu$M, 0.18 $\mu$M, 0.042 $\mu$M, 0.041 $\mu$M and 0.021 $\mu$M, respectively.

(4) Measurement of the Activity for Inhibiting Proliferation of the T Cells

Test was conducted by the method as disclosed in "Current Protocol in Immunology" [Edited by Coligan, et al., (1991)] Chapter 3, page 12 (Published from Willy Interscience, Inc.). After sacrificed a Balb/c strain male mouse, the spleen was enucleated and a suspension of the spleen cells in RPMI-1640 culture medium was prepared. Said suspension was filtered through a nylon fiber mesh, and subjected to a centrifugal separation (1,200 rpm, for 5 minutes), there were added on pellet 5 ml of 0.15 M ammonium chloride, 10 mM potassium hydrogencarbonate, and 0.1 mM disodium salt of EDTA (pH 7.2) per one spleen so as to suspend the cells, and the suspension was incubated at 37° C. for 5 minutes. A suitable amount of RPMI-1640 culture medium was added to the suspension, and this mixture was subjected to a centrifugal separation (1,200 rpm, for 5 minutes), the separated cells were washed, after repeated further washing operations twice, the cells were resuspended in RPMI-1640 culture medium containing 10% FBS (RPMI-10). After counted the number of cells by using a hemacytometer, a suspension containing cell density of $10^6$/ml was prepared by diluting with RPMI-10 culture medium. A test compound was dissolved in dimethyl sulfoxide to prepare a solution of $2 \times 10^{-2}$ M, then prepared 6 stages of 10-fold dilution sequences. Each one of these 10-fold dilution sequences was placed on a 96-well tissue culture plate in an amount of 10 $\mu$l/well (the final concentrations of test compounds: $10^{-9}$ to $10^{-4}$ M), and added the previously prepared cell suspension in an amount of 190 $\mu$l/well. There was added 40 $\mu$g/ml of Concanavaline A in an amount of 10 $\mu$l/well, and incubated at 37° for 2 days, under 5% carbon dioxide gas phase.

20 $\mu$Ci/ml of [methyl-$^3$H] thymidine was added in an amount of 10 $\mu$l/well, after further incubated overnight, by using a cell harvester the cells were recovered on the filter of the harvester. The filter was cut out from the cell harvester and put in a vial, then 5 ml of a scintillation cocktail (ACS-II) was added, and measured by using a liquid scintillation counter. By using the compound of Example 3 as test compound, IC$_{50}$ value was 2 $\mu$M.

(5) Determination of the Activity for Inhibiting Chronic Contactive Dermatitis

The activity for inhibiting chronic contactive dermatitis [J. Dermatol. Sci., Vol. 8, (1994), page 54] which is analogous to atopic dermatitis being reported by Kitagaki, et al. was discussed by using the method as follows. The right-side ear pinna of Balb/c strain male mouse was subjected to antigen sensitization by coating with 20 $\mu$l of acetone solution of 1% trinitrochlorobenzene (TNCB). 7 Days after the antigen sensitization, the same right-side pinna was subjected to antigen induction by coating with 20 $\mu$l of 1% TNCB acetone solution. The treatment of antigen induction was repeated in every 2 days so as to induced chronic contactive dermatitis. In this test, increase of thickness of the right-side ear pinna was induced by passing into a chronic state of the contactive dermatitis. The test compound was dissolved in acetone-methanol (4:1 by v/v) and 20 μl of this solution was administered by coating on the right-side of ear pinna once a day from 24th day after the antigen induction for 2 weeks. As to the control, the only the solvent was similarly administered. The antigen induction by the test compound during administration period was conducted at 30 minutes before the administration. The thickness of the ear pinna of 14th day after the administration was measured by a dial thickness gauge.

The results are shown in Table 36 as follows.

TABLE 36

| Concentration (%) of compound of Example 3 | Thickness of ear pinna (×10 μm) | Inhibition rate (%) |
|---|---|---|
| 0 (Control) | 137.1 ± 6.2 | — |
| 0.1 | 120.4 ± 5.3 | 12 |
| 0.3 | 105.0 ± 7.2 | 23 * |
| 1.0 | 64.5 ± 1.6 | 53 * |

* Significant difference between the control: $p < 0.01$ Dunnett's test
Number of the test animals: 8

(6) Determination of the Activity for Inhibiting TPA Induced Inflammation

Test was conducted by the modified method of Carlson, et al. [Agents Actions, Vol. 26, (1989), page 319]. Thus, to the ear pinna of ICR strain female mouse, 20 μl of acetone solution of 12-O-tetradecanoylphorbol-13-acetate (TPA) in the concentration of 200 μg/ml was coated to induce inflammation. The thickness of ear pinna of 4 hours after the TPA coating was measured, and difference of the last value was defined as the ear pinna inflammation. Test compound was dissolved in acetone-methanol (4:1 by v/v) to make the concentration of 1%. 20 μl of test compound solution was coated on the ear pinna 30 minutes before the TPA coating. By using compound of Example 3 as test compound, the inflammation was inhibited at the rate of 66%.

(7) Determination of the Activity for Inhibiting Proliferation of Rat Mesangial Cells In accordance with the method of F. Jaffer, et al. [Am. J. Pathol., Vol. 135, (1989), pages 261–269], the mesangial cells were collected. Under anesthetized condition, the kidney of a rat was aseptically enucleated and the medulla renis was cut out, then the cortex renis was pressed to a sieve (120 mesh) made of stainless steel. The fraction of cortex renis passed through the sieve was put on another sieve of 200 mesh and washed with PBS (phosphate-buffered saline), the fraction being remained on the sieve was confirmed as the glomerulus. This fraction was cultured in RPMI 1640 medium [containing 15% of fetal calf serum (FCS), and 5 μg/ml of insulin] for 4 weeks. This fraction was further subcultured twice, and the remaining cells were thought of as the mesangial cells for use of this experiment.

Determination of the activity for inhibiting proliferation of rat mesangial cells was conducted in accordance with the method of M. B. Ganz, et al. [Am. J. Physiol., Vol. 259, (1990), pages F269–F278].

Thus 2×10⁴/ml of mesangial cells were inoculated on a culture plate (48 wells, each well having the capacity of 0.5 ml), and cultured with RPMI medium (containing 15% FCS) for 3 days. The RPMI medium was then changed to another RPMI medium wherein the concentration of FCS was decreased to 0.5%, and further cultured for 3 days. Next, the RPMI medium was changed to another RPMI medium containing the same concentration of FCS, and added the test compound being dissolved in dimethyl sulfoxide (the final concentration of dimethyl sulfoxide was lower than 0.1%) and 5 ng/ml (the final concentration) of platelet-derivered growth factor BB (PDGF-BB). After 24 hours, 1 μCi/well of [³H]-thymidine was added, and incubated for additional 24 hours. The supernatant of the culture medium was taken up, and the amount of [³H]-thymidine up-taken into the cells was measured by use of scintillation counter. $IC_{50}$ value measured by using compound of Example 3 for the test was 0.79 μM.

We claim:

1. Benzimidazole derivatives or salts thereof represented by the general formula,

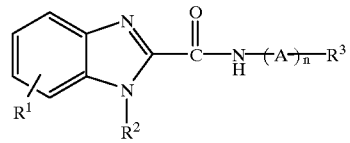

wherein
$R^1$ is a hydrogen atom or a halogen atom;
$R^2$ is a phenyl-lower alkyl group;
$R^3$ is a heterocyclic group selected from the group consisting of an indolyl group, indolinyl group, 1H-indazolyl group, 2(1H)-quinolinonyl group, 3,4-dihydro-2(1H)-quinolinonyl group and 3,4-dihydro-1,4(2H)-benzoxazinyl group, said heterocyclic group may have 1 to 3 substituents selected from the group consisting of: a group of the formula —B—$R^4$, wherein B is a lower alkylene group and $R^4$ is a 5- to 11-membered saturated or unsaturated heterocyclic group of single ring or binary ring, having 1 to 4 hetero atoms selected from the group consisting of a nitrogen atom, oxygen atom and sulfur atom, (said 5- to 11-membered heterocyclic group may have 1 to 3 substituents selected from the group consisting of a halogen atom, a lower alkyl group, a lower alkoxy group and an oxo group) or $R^4$ is a group of the formula —$NR^5R^6$, wherein $R^5$ and $R^6$ are each the same or different, and are a hydrogen atom, a lower alkyl group, a cycloalkyl group, a pyridylcarbonyl group, an isoxazolylcarbonyl group which may have 1 to 3 lower alkyl groups as substituents, a pyrrolylcarbonyl group or an amino-substituted lower alkyl group which may have a lower alkyl group as a substituent, further $R^5$ and $R^6$ may form a 5- to 6-membered saturated heterocyclic group by combining $R^5$ and $R^6$ together with the adjacent nitrogen atom being bonded thereto and with or without other nitrogen atom or oxygen atom, said 5- to 6-membered saturated heterocyclic group may have 1 to 3 substituents selected from the group consisting of a hydroxy group and a phenyl group; a lower alkenyl group; a lower alkoxycarbonyl group; a phenoxy-lower alkyl group which may have 1 to 3 cyano groups as substituents; a halogen-substituted lower alkyl group; and a lower alkoxycarbonyl-substituted lower alkyl group;

A is a lower alkylene group; and
n is 0 to 1.

2. The benzimidazole derivatives or salts thereof according to claim 1, wherein $R^3$ is an indolyl group.

3. The benzimidazole derivatives or salts thereof according to claim 1, where $R^3$ is an indolinyl group.

4. The benzimidazole derivatives or salts thereof according to claim 1, wherein $R^3$ is a 1H-indazolyl group.

5. The benzimidazole derivatives or salts thereof according to claim 1, wherein $R^3$ is a 2(1H)-quinolinonyl group, or a 3,4-dihydro-2(1H)-quinolinonyl group.

6. The benzimidazole derivatives or salts thereof according to claim 1, wherein $R^3$ is a 3,4-dihydro-1,4(2H)-benzoxazinyl group.

7. A process for preparing a benzimidazole derivative of the general formula (1), by reacting a benzimidazole compound of the formula (2) with an amine of the formula (3),

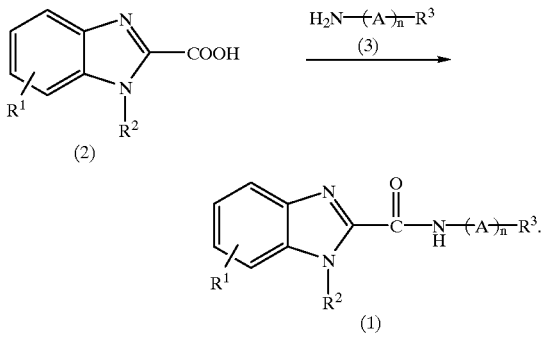

wherein $R^1$ is a hydrogen atom or a halogen atom;

$R^2$ is a phenyl-lower alkyl group;

$R^3$ is a heterocyclic group selected from the group consisting of an indolyl group, indolinyl group, 1H-indazolyl group, 2(1H)-quinolinonyl group, 3,4-dihydro-2(1H)-quinolinonyl group and 3,4-dihydro-1,4(2H)-benzoxazinyl group, said heterocyclic group may have 1 to 3 substituents selected from the group consisting of: a group of the formula —B—$R^4$, wherein B is a lower alkylene group and $R^4$ is a 5- to 11-membered saturated or unsaturated heterocyclic group of single ring or binary ring, having 1 to 4 hetero atoms selected from the group consisting of a nitrogen atom, oxygen atom and sulfur atom, (said 5- to 11-membered heterocyclic group may have 1 to 3 substituents selected from the group consisting of a halogen atom, a lower alkyl group, a lower alkoxy group and an oxo group) or $R^4$ is a group of the formula —$NR^5R^6$, wherein $R^5$ and $R^6$ are each the same or different, and are a hydrogen atom, a lower alkyl group, a cycloalkyl group, a pyridylcarbonyl group, an isoxazolylcarbonyl group which may have 1 to 3 lower alkyl groups as substituents, a pyrrolylcarbonyl group or an amino-substituted lower alkyl group which may have a lower alkyl group as a substituent further $R^5$ and $R^6$ may form a 5- to 6-membered saturated heterocyclic group by combining $R^5$ and $R^6$ together with the adjacent nitrogen atom being bonded thereto and with or without other nitrogen atom or oxygen atom, said 5- to 6-membered saturated heterocyclic group may have 1 to 3 substituents selected from the group consisting of a hydroxy group and a phenyl group; a lower alkenyl group; a lower alkoxycarbonyl group; a phenoxy-lower alkyl group which may have 1 to 3 cyano groups as substituents; a halogen-substituted lower alkyl group; and a lower alkoxycarbonyl-substituted lower alkyl group;

A is a lower alkylene group; and n is 0 to 1.

8. The benzimidazole derivatives or salts thereof according to claim 2, wherein $R^1$ is a hydrogen atom; and n is 0.

9. The benzimidazole derivatives or salts thereof according to claim 2, wherein $R^1$ is a hydrogen atom; and n is 1.

10. The benzimidazole derivatives or salts thereof according to claim 2, wherein $R^1$ is a halogen atom; and n is 0.

11. The benzimidazole derivatives or salts thereof according to claim 2, wherein $R^1$ is a halogen atom; and n is 1.

12. The benzimidazole derivatives or salts thereof according to claim 3, wherein $R^1$ is a hydrogen atom; and n is 0.

13. The benzimidazole derivatives or salts thereof according to claim 3, wherein $R^1$ is a hydrogen atom; and n is 1.

14. The benzimidazole derivatives or salts thereof according to claim 3, wherein $R^1$ is a halogen atom; and n is 0.

15. The benzimidazole derivatives or salts thereof according to claim 3, wherein $R^1$ is a halogen atom; and n is 1.

16. The benzimidazole derivatives or salts thereof according to claim 4, wherein $R^1$ is a hydrogen atom; and n is 0.

17. The benzimidazole derivatives or salts thereof according to claim 4, wherein $R^1$ is a hydrogen atom; and n is 1.

18. The benzimidazole derivatives or salts thereof according to claim 4, wherein $R^1$ is a halogen atom; and n is 0.

19. The benzimidazole derivatives or salts thereof according to claim 4, wherein $R^1$ is a halogen atom; and n is 1.

20. The benzimidazole derivatives or salts thereof according to claim 5, wherein $R^1$ is a hydrogen atom; and n is 0.

21. The benzimidazole derivatives or salts thereof according to claim 5, wherein $R^1$ is a hydrogen atom; and n is 1.

22. The benzimidazole derivatives or salts thereof according to claim 5, wherein $R^1$ is a halogen atom; and n is 0.

23. The benzimidazole derivatives or salts thereof according to claim 5, wherein $R^1$ is a halogen atom; and n is 1.

24. The benzimidazole derivatives or salts thereof according to claim 6, wherein $R^1$ is a hydrogen atom; and n is 0.

25. The benzimidazole derivatives or salts thereof according to claim 6, wherein $R^1$ is a hydrogen atom; and n is 1.

26. The benzimidazole derivatives or salts thereof according to claim 6, wherein $R^1$ is a halogen atom; and n is 0.

27. The benzimidazole derivatives or salts thereof according to claim 6, wherein $R^1$ is a halogen atom; and n is 1.

28. The benzimidazole derivatives or salts thereof according to any one of claims 8 to 27, wherein the 5- to 11-membered saturated or unsaturated single ring or binary ring heterocyclic group represented by the group of $R^4$ is a pyrrolidinyl, piperidinyl, piperazinyl, morpholino, thiomorpholino, pyridyl, homopiperazinyl, 1,2,5,6-tetrahydropyridyl, thienyl, quinolinyl, 1,4-dihydroquinolinyl, benzothiazolyl, pyrazinyl, pyrimidinyl, pyridazinyl, pyrrolyl, carbostyril, 3,4-dihydrocarbostyril, 1,2,3,4-tetrahydroquinolinyl, indolyl, isoindolyl, indolinyl, benzimidazolyl, benzoxazolyl, imidazolidinyl, isoquinolinyl, quinazolidinyl, 1,2,3,4-tetrahydroisoquinolinyl, 1,2-dihydroisoquinolinyl, quinoxalinyl, cinnolinyl, phthalazinyl, 1,2,3,4-tetrazolyl, 1,2,4-triazolyl, chromanyl, isoindolinyl, isochromanyl, pyrazolyl, imidazolyl, pyrazolidinyl, imidazo[1,2-a]pyridyl, benzofuryl, 2,3-dihydrobenzo[b]furyl, benzothienyl, 1-azacycloheptyl, 4H-chromenyl, 1H-indazolyl, 2-imidazolinyl, 2-pyrrolinyl, furyl, oxazolyl, oxazolidinyl, isoxazolyl, thiazolyl, isothiazolyl, pyranyl, pyrazolidinyl, 2-pyrazolinyl, quinuclidinyl, 1,4-benzoxazinyl, 3,4-dihydro-2H-1,4-benzoxazinyl, 3,4-dihydro-2H-1,4-benzothiazinyl, 1,4-benzothiazinyl, 1,2,3,4-tetrahydroquinoxalinyl, 1,3-dithia-2,4-dihydronaphthalenyl, tetrahydro-1,3-oxazinyl, tetrahydroxazolyl or 1,4-dithianaphthalenyl group.

29. The benzimidazole derivatives or salts thereof according to any one of claims 8 to 27, wherein the heterocyclic group represented by the group of $R^4$ is an imidazolyl group, pyrazolyl group or 1,2,4-triazolyl group.

30. The benzimidazole derivatives or salts thereof according to any one of claims 8 to 27, wherein $R^4$ is a group of the formula —$NR^5R^6$.

31. 1-Benzyl-6-chloro-2-{1-[3-(imidazol-1-yl)propyl]indol-5-ylaminocarbonyl}benzimidazole.

32. 1-Benzyl-6-chloro-2-{1-[3-(N-cyclohexyl-N-methylamino)propyl]indol-5-ylaminocarbonyl}-benzimidazole.

33. 1-Benzyl-6-chloro-2-{1-[3-(pyrazol-1-yl)propyl]indol-5-ylaminocarbonyl}benzimidazole.

34. 1-Benzyl-6-chloro-2-{1-[3-(1,2,4-triazol-1-yl)propyl]indol-5-ylaminocarbonyl}benzimidazole.

35. 1-Benzyl-6-chloro-2-{1-[3-(3,5-dimethylisoxazol-4-ylcarbonylamino)propyl]indol-5-ylaminocarbonyl}benzimidazole.

36. 1-Benzyl-6-chloro-2-{1-[3-(4-phenyl-4-hydroxypiperidin-1-yl)propyl]indol-5-ylaminocarbonyl}-benzimidazole.

37. 1-Benzyl-6-chloro-2-{4-[3-(pyridin-2-ylcarbonylamino)propyl]-3,4-dihydro-1,4(2H)-benzoxazin-7-ylaminocarbonyl}benzimidazole.

38. A pharmaceutical composition for inhibiting the enzymatic activity, of cGMP PDE containing, as the active ingredient, an effective amount of a benzimidazole derivative or a pharmaceutically acceptable salt thereof as claimed in claim 1.

39. A pharmaceutical composition for inhibiting proliferation of the cells containing, as the active ingredient, an effective amount of a benzimidazole derivative or a pharmaceutically acceptable salt thereof as claimed in claim 1.

40. A pharmaceutical composition for inhibiting synthesis and secretion of collagen containing, as the active ingredient, an effective amount of a benzimidazole derivative or a pharmaceutically acceptable salt thereof as claimed in claim 1.

41. An immunosuppressive agent containing, as the active ingredient, an effective amount of a benzimidazole derivative or a pharmaceutically acceptable salt thereof as claimed in claim 1.

42. An antiinflammatory agent containing, as the active ingredient, an effective amount of a benzimidazole derivative or a pharmaceutically acceptable salt thereof as claimed in claim 1.

* * * * *